US009211278B2

(12) United States Patent
Yang et al.

(10) Patent No.: US 9,211,278 B2
(45) Date of Patent: Dec. 15, 2015

(54) COMPOSITION CONTAINING ARYLNAPHTHALENE LIGNAN DERIVATIVE FOR PREVENTING AND/OR TREATING DEMENTIA

(71) Applicants: KOREA INSTITUTE OF SCIENCE AND TECHNOLOGY, Seoul (KR); The Council for Scientific and Industrial Research, Pretoria (ZA)

(72) Inventors: Hyun Ok Yang, Seoul (KR); Sung-Kwon Chung, Seoul (KR); Hak Cheol Kwon, Seoul (KR); Jin Wook Cha, Incheon (KR); Young-Joo Kim, Seoul (KR); Gerda Fouche, Pretoria (ZA); Rudzani Nthambeleni, Pretoria (ZA); Dashnie Naidoo, Pretoria (ZA); Jeremiah Senabe, Pretoria (ZA); Vinesh Jaichand Maharaj, Pretoria (ZA); Eric Khorombi, Pretoria (ZA); Jungyeob Ham, Gangneung (KR); Joon Ki Kim, Gunpo (KR)

(73) Assignees: KOREA INSTITUTE OF SCIENCE AND TECHNOLOGY, Seoul (KR); CSIR, Pretoria (ZA)

( * ) Notice: Subject to any disclaimer, the term of this patent is extended or adjusted under 35 U.S.C. 154(b) by 0 days.

(21) Appl. No.: 14/036,810

(22) Filed: Sep. 25, 2013

(65) Prior Publication Data

US 2014/0088186 A1    Mar. 27, 2014

(30) Foreign Application Priority Data

Sep. 26, 2012   (KR) .................. 10-2012-0107322

(51) Int. Cl.
| | | |
|---|---|---|
| *A01N 43/30* | (2006.01) | |
| *A61K 31/36* | (2006.01) | |
| *A61K 31/365* | (2006.01) | |
| *A23L 1/30* | (2006.01) | |
| *A23L 2/52* | (2006.01) | |
| *A61K 36/185* | (2006.01) | |

(52) U.S. Cl.
CPC ............ *A61K 31/365* (2013.01); *A23L 1/3002* (2013.01); *A23L 2/52* (2013.01); *A61K 36/185* (2013.01)

(58) Field of Classification Search
None
See application file for complete search history.

(56) References Cited

U.S. PATENT DOCUMENTS

| 7,179,484 B2 | 2/2007 | Singh | |
|---|---|---|---|
| 2007/0155771 A1* | 7/2007 | Rubinsztein et al. | ......... 514/291 |
| 2009/0202662 A1* | 8/2009 | Fouche et al. | ................ 424/725 |

FOREIGN PATENT DOCUMENTS

| JP | 2008-534582 | 8/2008 |
|---|---|---|
| KR | 10-0404719 | 11/2003 |
| WO | WO 2007/138531 A1 | 12/2007 |

OTHER PUBLICATIONS

CAS RN: 25001-57-4 (entered Nov. 16, 1984).*
Su et al., "Justicidin A inhibits AKT/mTOR and activates type III PI3K/beclin 1 signaling pathways leading to autophagy of human colorectal cancer cells," The Journal of the Federation of American Societies for Experimental Biology, Apr. 2010.*
Alphonse Probst et al., "Alzheimer's Disease: A Description of the Structural Lesions", Brain Pathology, vol. 1, 1991, pp. 229-239.
Lars H. Breimer et al., "Alzheimer Amyloid Aspects", Scientific Correspondence, Nature vol. 326, Apr. 23, 1987, pp. 749-750.
Robert Vassar et al., "Aβ-Generating Enzymes: Recent Advances in β- and γ-Secretase Research" Neuron, vol. 27, Sep. 2000, pp. 419-422.
Dennis J. Selkoe, "Alzheimer's Disease is a Synaptic Failure", Science, vol. 298, Oct. 25, 2002, pp. 789-791 with cover page.
Peer-Hendrik Kuhn et al., "ADAM10 is the Physiologically Relevant, Constitutive α-Secretase of the Amyloid Precursor Protein in Primary Neurons", The EMBO Journal, vol. 29, No. 17, 2010, pp. 3020-3032.
Katsura Munakata et al., "Justicidin A and B, the Fish-Killing Components of *Justicia hayatai* Var. *decumbens*", Tetrahedron Letters, No. 47, 1965, pp. 4167-4170.
Antonio C. Siani et al., "5-Methoxyjusticidin A, a New Arylnaphthalene Lignan from *Protium unifoliolatum*" J. Nat. Prod., No. 61, 1998, pp. 796-797.
Chien-Chih Chen et al., "Antiplatelet Arylnaphthalide Lignans from *Justicia procumbens*" J. Nat. Prod., No. 59, 1996, pp. 1149-1150.
Extended European Search Report mailed Dec. 3, 2013 in corresponding European Application No. 13185993.6.
"Revista Brasileira de Farmacognosia", Brazilian Journal of Pharmacognosy, Elsevier, p. 1.
T. A. Henry et al., "Observations on Reputed Dysentery Remedies", Transactions of the Royal Society of Tropical Medicine and Hygiene, Elsevier, GB, vol. 17, No. 6, Dec. 13, 1923, pp. 378-385.
Margaret Roberts, "Indigenous Healing Plants", Southern Book Publishers, 1990, pp. 81-82 with cover pages.
H. M. Burkill, "The Useful Plants of West Tropical Africa", Royal Botanic Gardens Kew, vol. 2, 1994, p. 167 with cover pages.
Extended European Search Report mailed Nov. 13, 2013 in Application No. 13185164.4.

(Continued)

*Primary Examiner* — Anna Pagonakis
*Assistant Examiner* — Jared D Barsky
(74) *Attorney, Agent, or Firm* — Staas & Halsey LP

(57) ABSTRACT

Composition and method for preventing and/or treating dementia and ameliorating memory impairment and/or improving memory, comprising one or more arylnaphthalene lignan derivatives, namely Justicidin A, 5-methoxyjusticidin A, Chinensinaphthol, and a pharmaceutically-acceptable salt thereof, as active ingredient.

1 Claim, 22 Drawing Sheets

(56) References Cited

OTHER PUBLICATIONS

Ichikawa, "AFlora The Database of Plant Utilization in Africa", The Center for African Area Studies, Kyoto University, (Online, 2014) p. 1.

U.S. Office Action mailed on Jan. 7, 2015 in U.S. Appl. No. 14/038,378.

U.S. Office Action mailed on Mar. 27, 2015 in U.S. Appl. No. 14/038,378.

U.S. Office Action mailed on Jun. 10, 2015 in U.S. Appl. No. 14/038,378.

U.S. Appl. No. 14/038,378, filed Sep. 25, 2013, Hyun Ok Yang et al., (1) Korea Institute of Science and Technology (2) CSIR.

* cited by examiner

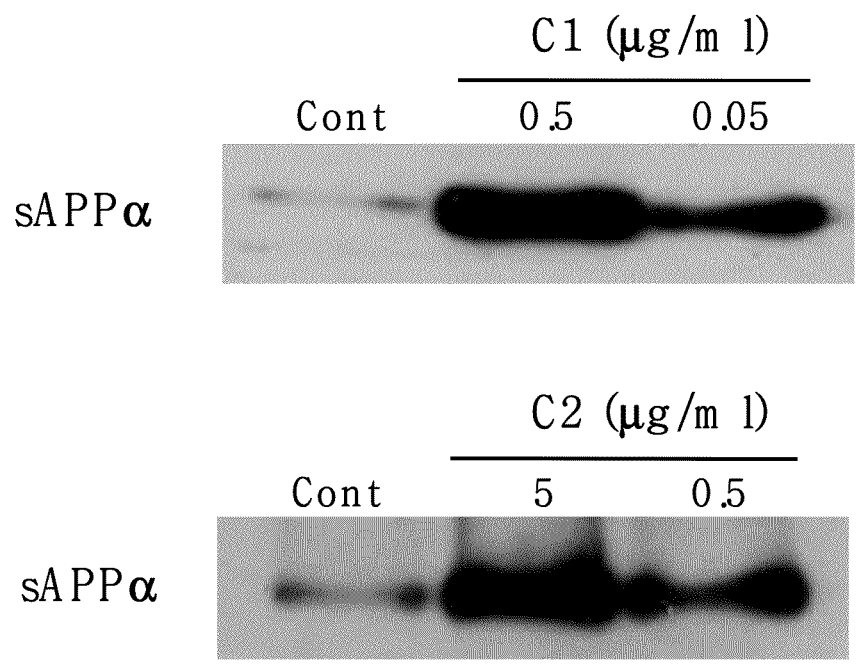

* Significantly different (P<0.05) from Normal group
+ Significantly different (P<0.05) from Scopolamine group

*,** Significantly different (P<0.05, P<0.01) from Scopolamine group

Memory Index (%) = [Exploring time on novel object / Total exploring time] X 100

*, , * Significantly different (P<0.05, P<0.01, P<0.001) from Normal group
, ## Significantly different (P<0.05, P<0.01) from Scopolamine group

COMPOSITION CONTAINING ARYLNAPHTHALENE LIGNAN DERIVATIVE FOR PREVENTING AND/OR TREATING DEMENTIA

CROSS-REFERENCE TO RELATED APPLICATIONS

This application claims the benefit of Korean Patent Application No. 10-2012-0107322, filed on Sep. 26, 2012, in the Korean Intellectual Property Office, the entire disclosure of which is incorporated herein by reference.

BACKGROUND OF THE INVENTION

1. Field of the Invention

The present invention relates to a composition or a method for preventing treating, improving and/or ameliorating a disease associated with β-amyloid in brain which is at least one selected from dementia, ameliorating memory impairment and memory, by using a composition including arylnaphthalene lignan derivative, in particular, Justicidin A, 5-methoxyjusticidin A, Chinensinaphthol and/or a pharmaceutically-acceptable salt thereof.

2. Description of the Related Art

Generally, dementia is a symptom showing remarkably decreased brain functions such as the abilities of memory, thinking, understanding, calculating, learning, language, and judgment where the brain normal cell is damaged due to various reasons.

In particular, Alzheimer's disease is a most important disease of senile dementia, and is mainly caused by the accumulation of β-amyloid in brain and its neurotoxicity (Probst A. et al., Brain Pathol., 1:229-239, 1991). It has been reported that β-amyloid makes the protein plaque in brain, thereby causing the occurrence of Alzheimer's disease (Breimer L H, et al. Nature, 326: 749-750, 1987).

β-amyloid is formed by the sequential interaction of amyloid precursor protein (APP) with β-secretase (BACE1) and gamma-secretase (Vassa and Citron, Neuron 27, 419-422, 2000). β-amyloid is largely classified into two types of Aβ40 of 40 amino acids and Aβ42 of 42 amino acids. β-amyloid is mainly Aβ40, but relatively small amounts of Aβ42 makes the plaque formation easier and thus is considered as a factor causing the disease (Selkoe, Science 298: 789-891, 2002).

The cleavage of APP is caused by two different enzymes of alpha-secretase and beta-secretase, which have opposite control activities in the formation of beta-amyloid. Beta-secretase acts largely on the formation of Aβ42 and APP-β, while alpha-secretase results in the formation of APP-α having a neuron protecting activity and reduces the formation of beta-amyloid relatively. Unlike the beta-secretase, organic compounds with low molecular weight which activate the alpha-secretase have not been researched as yet, and the studies on the identification and mechanism for the alpha-secretase are on-going at a molecular level (Kuhn et al, EMBO Journal, 2010, 29, 3020). Accordingly, the alpha-secretase draws an attention as a new molecular target for developing a drug treating Alzheimer's disease.

The commercially available representative drugs for treating dementia are tacrine (Cognex, 1994) and donepezil (Aricept, 1996) used after U.S. FDA approval. The mechanism of drugs to prevent and treat the dementia has been known to increase the concentration of the neurotransmitter acetylcholine by inhibiting the activity of acetylcholinesterase AChE degrading the acetylcholine. However, tacrine has serious hepatotoxicity. Donepezil does not have hepatotoxicity, but causes various side-effects such as nausea, anorexia, diarrhea, and etc. by stimulating the parasympathetic nerve.

Therefore, a new drug for treating dementia which can treat the causes of disease without the side-effects is still needed and has been studied actively. As a part of the studies, there are efforts to develop continuously a drug for inhibiting the β-amyloid formation.

Justicidin A having arylnaphthalene lignan structure was separated as an active ingredient of fish poison of Justicia hayatai for the first time (Munakata et al, *Tetrahedron Letters*, 1965, (47), 4167). Justicidin A was subsequently separated from various sources and showed different activities. However, Justicidin A has not been reported to have an effect for preventing and/or treating dementia, and improving the memory function.

5-methoxyjusticidin A is a derivative of arylnaphthalene lignan. It was reported in Protium unifoliolatum for the first time (Sian et al, J. Nat. Prod. 1998, 61, 796), but the efficacy was not reported at all.

Chinensinaphthol, an arylnaphthalene lignan derivative was reported in Justicia procumbens (Chen et al, J. Nat. Prod. 1996, 59, 1149), but has not been reported to have any efficacy on the memory, brain disorder, or dementia.

Particularly, it has not been reported or known nearly that hundreds of arylnaphthalene lignan or derivatives thereof including Justicidin A, 5-methoxyJusticidin A, and Chinensinaphthol have an effect on the memory, brain disorder, or dementia.

SUMMARY OF THE INVENTION

While the present inventors researched a new drug for treating dementia which can treat the causes of disease without any side-effect, they identified that arylnaphthalene lignan or derivatives thereof including Justicidin A, 5-methoxyjusticidin A, and Chinensinaphthol had an effect on prevention and/or treatment for dementia by inhibiting the formation of beta-amyloid, and completed the present invention. In addition, the present inventors found that the arylnaphthalene lignan or derivatives thereof had an effect on prevention and/or treatment for dementia by performing the sequential actions of increasing APP-α production by alpha-secretase, activating alpha-secretase, and inhibiting the formation of beta-amyloid. As a result of the experiments of Morris water-maze test and Novel object recognition test in the model mouse which had an impaired memory driven with scopolamine treatment, they found that Justicidin A, 5-methoxyJusticidin A, and Chinensinaphthol improved the memory impairment, and completed the present invention.

In an embodiment, it is an object to provide a composition for preventing, treating, improving and/or ameliorating a condition associated with β-amyloid in brain, comprising at least one selected from the group consisting of arylnaphthalene lignan derivatives and pharmaceutically acceptable salts thereof as an active ingredient.

In an embodiment of the present invention, it is an object to provide a pharmaceutical composition for preventing and/or treating dementia, comprising one or more selected from the group consisting of Justicidin A represented by Chemical Formula 1, 5-methoxyjusticidin A represented by Chemical Formula 2, Chinensinaphthol represented by Chemical Formula 3, and a pharmaceutically acceptable salt thereof, as an active ingredient:

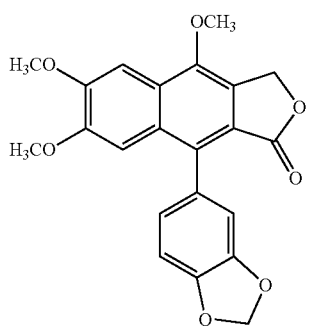

<Chemical Formula 1>

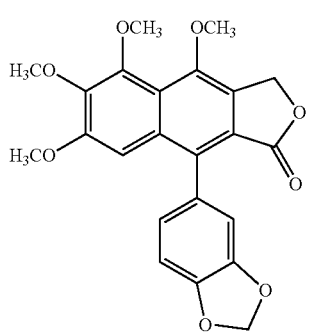

<Chemical Formula 2>

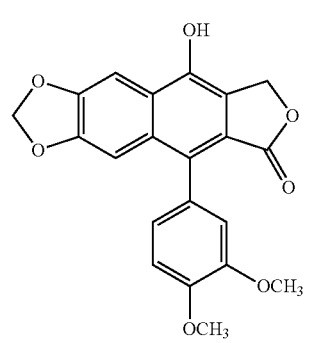

<Chemical Formula 3>

In another embodiment, it is an object to provide a food composition for preventing or improving a dementia, comprising one or more selected from the group consisting of Justicidin A represented by Chemical Formula 1, 5-methoxyjusticidin A represented by Chemical Formula 2, Chinensinaphthol represented by Chemical Formula 3, and a pharmaceutically acceptable salt thereof.

In still another embodiment, it is an object to provide a pharmaceutical composition for ameliorating memory impairment or improving a memory, comprising one or more selected from the group consisting of Justicidin A represented by Chemical Formula 1, 5-methoxyjusticidin A represented by Chemical Formula 2, Chinensinaphthol represented by Chemical Formula 3, and a pharmaceutically acceptable salt thereof, as an active ingredient.

In still another embodiment, it is an object to provide a food composition for ameliorating memory impairment or improving memory, comprising one or more selected from the group consisting of Justicidin A represented by Chemical Formula 1, 5-methoxyjusticidin A represented by Chemical Formula 2, Chinensinaphthol represented by Chemical Formula 3, and a pharmaceutically acceptable salt thereof.

In still another embodiment, it is an object to provide a method of separating and purifying Justicidin A represented by Chemical Formula 1, 5-methoxyjusticidin A represented by Chemical Formula 2, and Chinensinaphthol represented by Chemical Formula 3 from a herbal extract.

In another embodiment, it is to provide a method for inhibiting the formation of beta-amyloid using the arylnaphthalene lignan or derivatives. Specifically, an embodiment relates to a method of performing the sequential actions of increasing APP-α production by alpha-secretase, activating alpha-secretase, and inhibiting the formation of beta-amyloid.

In still another embodiment is to provide a method for preventing and/or treating dementia, ameliorating memory impairment and/or improving memory, comprising arylnaphthalene lignin or derivatives. prevention and/or treatment for dementia by performing the sequential actions of increasing APP-α production by alpha-secretase, activating alpha-secretase, and inhibiting the formation of beta-amyloid.

In another embodiment, it is an object to provide a use of arylnaphthalene lignan or its derivatives for preventing and/or treating dementia, ameliorating memory impairment and/or improving memory.

BRIEF DESCRIPTION OF THE DRAWINGS

FIG. 5 shows the increased production of alpha-secretase product (sAPP) at various concentration of Justicidin A or 5-methoxyjusticidin A (Cont: negative control).

DETAILED DESCRIPTION OF THE INVENTION

Figure 1A:
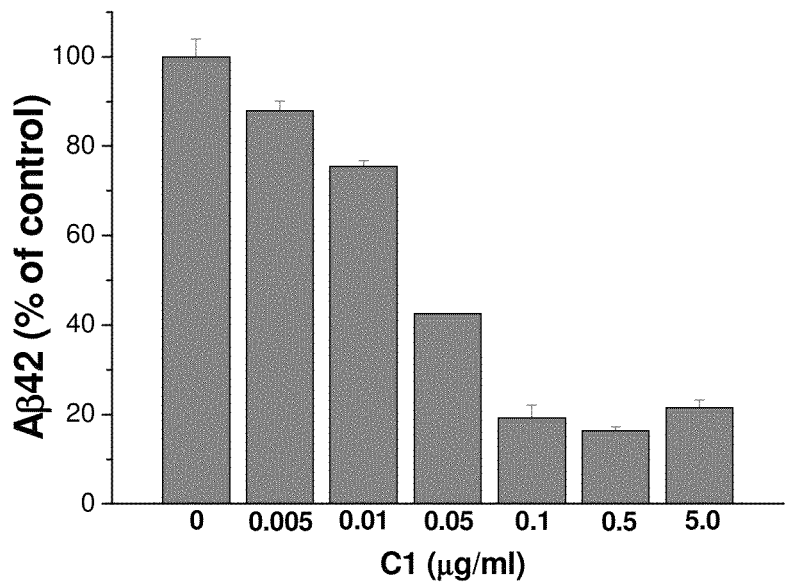
FIGS. 1a and 1b are graphs showing the inhibitory effect on the formation of beta-amyloid at various concentrations of added Justicidin A (C1) obtained in Example 2 (Aβ42 in upper; Aβ40 in lower, and 0: negative control).

The present invention provides new uses of preventing and/or treating dementia, and, ameliorating and/or improving memory impairment of arylnaphthalene lignan derivatives such as Justicidin A, 5-methoxyJusticidin A, and Chinensinaphthol.

An embodiment of the present invention provides a pharmaceutical composition for preventing and/or treating dementia, comprising arylnaphthalene lignan derivatives and pharmaceutically acceptable salts thereof as an active ingredient.

Another embodiment provides a method for inhibiting the formation of beta-amyloid comprising administering a therapeutically effective amount of arylnaphthalene lignan derivatives and pharmaceutically acceptable salts thereof, to a subject in need.

Further embodiment provides a method of increasing APP-α production comprising administering a therapeutically effective amount of arylnaphthalene lignan derivatives and pharmaceutically acceptable salts thereof, to a subject in need.

Still further embodiment provides a method for preventing, treating, improving and/or ameliorating a disease or condition associated with beta-amyloid in brain, for examples dementia, memory and/or memory impairment, comprising administering a therapeutically effective amount of arylnaphthalene lignan derivatives and pharmaceutically acceptable salts thereof, to a subject in need.

As used herein, the term "and/or," when used in a list of two or more items, means that any one of the listed items can be employed by itself, or any combination of two or more of the listed items can be employed.

More specifically, a pharmaceutical composition for preventing and/or treating dementia, comprising one or more selected from the group consisting of Justicidin A represented by Chemical Formula 1, 5-methoxyjusticidin A represented by Chemical Formula 2, Chinensinaphthol represented by Chemical Formula 3, and pharmaceutically acceptable salts thereof, as an active ingredient, is provided:

<Chemical Formula 1>

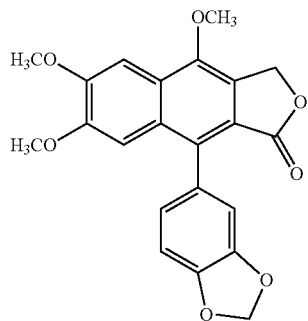

<Chemical Formula 2>

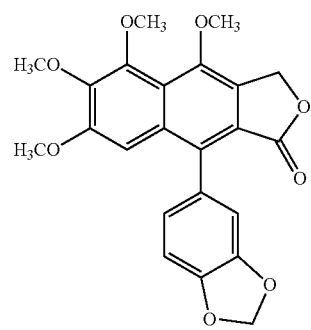

<Chemical Formula 3>

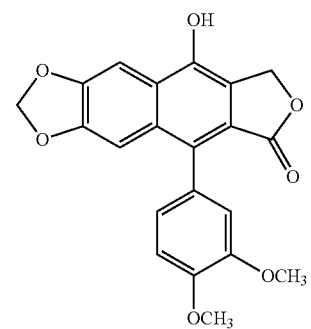

Another embodiment provides a food composition for preventing and/or improving dementia, comprising one or more selected from the group consisting of Justicidin A represented by Chemical Formula 1, 5-methoxyjusticidin A represented by Chemical Formula 2, and Chinensinaphthol represented by Chemical Formula 3, and a pharmaceutically acceptable salt thereof.

In another embodiment provides a pharmaceutical composition for ameliorating memory impairment or improving memory comprising selected from the group consisting of Justicidin A represented by Chemical Formula 1, 5-methoxyjusticidin A represented by Chemical Formula 2, and Chinensinaphthol represented by Chemical Formula 3, and/or a pharmaceutically acceptable salt thereof, is provided.

In still another embodiment provides a food composition for ameliorating memory impairment or improving a memory comprising one or more selected from the group consisting of Justicidin A represented by Chemical Formula 1, 5-methoxyjusticidin A represented by Chemical Formula 2, and Chinensinaphthol represented by Chemical Formula 3, and/or a pharmaceutically acceptable salt thereof, is provided.

Another embodiment is to provide arylnaphthalene lignan or its derivative for use in prevention, treatment, improvement and/or amelioration of a condition associated with β-amyloid in brain, wherein the arylnaphthalene lignan derivative is at least one selected from the group consisting of Justicidin A represented by Chemical Formula 1, 5-methoxyjusticidin A represented by Chemical Formula 2, and Chinensinaphthol represented by Chemical Formula 3.

The present inventors identified that Justicidin A, 5-methoxyJusticidin A, and Chinensinaphthol had an excellent effect on inhibiting the formation of beta-amyloid (see Experimental Examples 1 and 5), and thus developed their use for prevention and/or treatment for dementia.

In an experiment of the present invention, Justicidin A or 5-methoxyjusticidin A was injected into HeLa cell line transfected with amyloid precursor protein (APP) and the result showed their inhibitory effect on the beta-amyloid formation (see Experimental Example 1).

To examine specifically the cause of inhibiting the beta-amyloid formation, the present inventors measured the degree of beta-secretase activity. As a result, Justicidin A and 5-methoxyjusticidin A did not inhibit the activity of beta-secretase at all. As a result of the production degree of product formed by alpha-secretase (sAPPα), the production (sAPPβ) was notably increased by the treatment of Justicidin A and 5-methoxyjusticidin A. Therefore, it is confirmed that Justicidin A and 5-methoxyjusticidin A activated the alpha-secretase, increased the formation of sAPPα and then inhibited the formation of beta-amyloid.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject", refers to an animal, preferably a mammal, and most preferably a human both male and female, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "pharmaceutically acceptable salts" shall mean non-toxic salts of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Therefore, the term "a patient in need of treatment" as used herein will refer to any subject or patient who currently has or may develop dementia, memory or memory impairment which can be treated by arylnaphthalene lignans represented by Formula 1 to 3, or in combination with another therapeutic intervention including but not limited to another medication.

The term "treating" or "treatment" as used herein, refers to any indicia of success in the prevention and/or treatment, amelioration of dementia, memory or memory impairment and modification of dementia, including any objective or subjective parameter such as abatement; remission; diminishing of memory or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the compounds or agents of the present invention for treatment of any form of dementia in both males and females. In some instances, treatment with the compounds of the present invention will done in combination with other compounds to prevent, inhibit, or arrest the progression of the dementia.

The term "therapeutic effect" as used herein, refers to the effective improvement in or reduction of symptoms of dementia. The term "a therapeutically effective amount" as used herein means a sufficient amount of one or more of the compounds of the invention to produce a therapeutic effect, as defined above, in a subject or patient in need of such dementia treatment.

The terms "subject" or "patient" are used herein interchangeably and as used herein mean any mammal including but not limited to human beings including a human patient or subject to which the compositions of the invention can be administered. The term mammals include human patients, both male and female and non-human primates, as well as experimental animals such as rabbits, rats, mice, and other animals.

To prove that the inhibitory effect of Justicidin A, and 5-methoxyJusticidin A on the beta-amyloid formation is dependent on the chemical structure, the present inventors compared with the inhibitory effect of lignan compounds which included a similar structure to those of the Justicidin A, 5-methoxyJusticidin A and Chinensinaphthol, or γ-lactone, and the inhibitory effect of the Justicidin A, 5-methoxyjusticidin A and Chinensinaphthol.

Retrochinensinaphthol methylether of Chemical Formula 4, and Succilactone of Chemical Formula 5 were separated from the *Monsonia angustifolia* extract produced in Experimental Example 1. Justicidin G of Chemical Formula 6 was purchased from ChromaDex Inc (00010550), Justicidin F of Chemical Formula 7 was purchased from ChromaDex Inc (00020012) and Justicidin D of Chemical Formula 8 was purchased from ChromaDex Inc. (00012176).

<Chemical Formula 4>

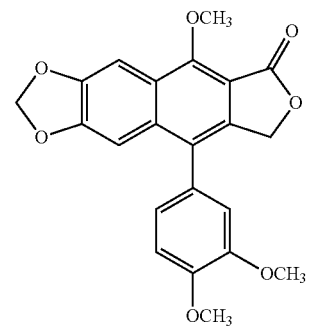

<Chemical Formula 5>

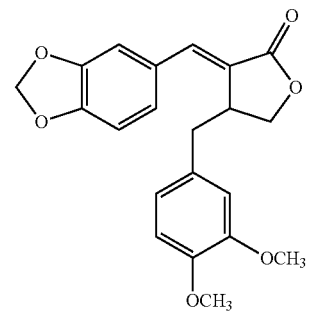

-continued

<Chemical Formula 6>

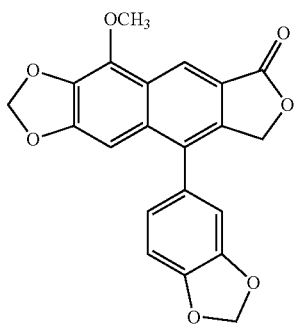

<Chemical Formula 7>

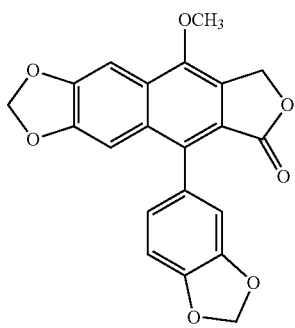

<Chemical Formula 8>

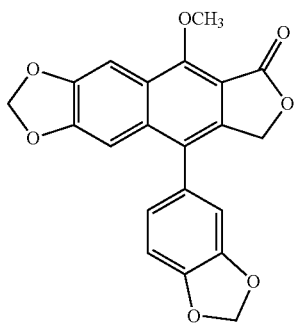

The arylnaphthalene lignans represented by Chemical Formulae 4 to 8 and a lignan lactone represented by Chemical Formula 5 were measured for inhibiting the formation of beta-amyloid. Compared with the inhibitory effects of Justicidin A, 5-methoxyJusticidin A, and Chinensinaphthol, the inhibitory effects of arylnaphthalene lignans and lignan lactone did not show the notable effect (see FIGS. 6a and 6b).

The result confirmed that the inhibitory effect of Justicidin A, 5-methoxyJusticidin A and Chinensinaphthol having the arylnaphthalene lignan structure showed the dependency on the specific chemical structure.

As described above, Justicidin A, 5-methoxyJusticidin A, and/or Chinensinaphthol have activities effectively inhibiting the formation of beta-amyloid (Aβ40, Aβ42) which has been known as a causing factor of dementia, particularly Alzheimer's disease, thus can be used for preventing or treating dementia as an active agent.

The dementia-relating diseases of the present invention preferably includes Alzheimer's disease, but not limited thereto.

In addition, Justicidin A of Chemical Formula 1 which was a representative arylnaphthalene lignan derivatives was tested for an effect of improving the memory impairment in the model mouse having an impaired memory induced by scopolamine treatment. And the effect was identified improving the memory.

The arylnaphthalene lignan derivatives such as Justicidin A, 5-methoxyJusticidin A, and/or Chinensinaphthol can be used as themselves or pharmaceutical salts thereof, and preferably pharmaceutical acceptable salts. The preferable example of salts can be acid addition salt which is prepared by a pharmaceutically acceptable free acid. The free acid can be organic acid or inorganic acid. The examples of organic acids include citric acid, acetic acid, lactic acid, tartaric acid, maleic acid, fumaric acid, formic acid, propionic acid, oxalic acid, trifluoroacetic acid, benzoic acid, gluconic acid, methasulphonic acid, succinic acid, 4-toluenesulphonic acid, glutamic acid, and aspartic acid, but not limited thereto. The examples of inorganic acids include hydrochloric acid, bromic acid, sulfuric acid and phosphathic acid, but not limited thereto.

The arylnaphthalene lignan derivatives can be prepared by separating from a natural product containing the derivatives according to the extraction and separation method known in the art, or by synthesizing according to known chemical synthesis method (Munakata et al, Tetrahedron Lett. 1965, (47), 4167; Yu et al, Med. Chem. Res. 2010, 19, 71)

The amount of arylnaphthalene lignan derivatives which inhibit the formation of beta-amyloid as active ingredient of composition can be determined in considering the method and object to be used, the condition of subject, the kind and the severity of condition, and the like, and for example, can be 0.00001 to 99.9 wt %, or preferably 0.001 to 50 wt % with respect to the total weight of the composition, but not limited thereto.

The pharmaceutical composition can be administered to a mammal including a human according to various routes of administration. The routes of administration can be any conventional route normally used to administer a medicament, and for examples the composition can be administered orally, rectally, intravenously, intramuscularly, intradermally, endometrially and intracerebroventricularly. The pharmaceutical composition can be formulated according to the conventional formulating method in formulation of oral forms including powder, granule, tablet, capsule, suspension, emulsion, syrup, and aerosol, or parenteral forms including transdermal, suppository, and sterile intravenous forms.

The pharmaceutical composition can include pharmaceutically-applicable and physiologically-acceptable additives such as carriers, excipients and diluents as well as arylnaphthalene lignan derivatives. The carriers, excipients and diluents applicable to the pharmaceutical composition of the present invention include lactose, dextrose, sucrose, sorbitol, mannitol, xylitol, erythrytol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxylbenzoate, talc, magnesium stearate, mineral oil and the like. In the formulation of the composition, excipients and diluents used generally such as filling agent, extending agent, binding agent, wetting agent, disintegrating agent, surfactant, and the like can be added. The solid formulations for oral administration include tablet, pill, powder, granule, capsule and the like, and can be prepared by mixing with at least excipients such as starch, calcium carbonate, sucrose, lactose, gelatin and the like. Besides simple excipients, the lubricants such as magnesium stearate, talc and the like can be added. In a liquid solution for oral administration including suspension, solution, emulsion, syrup and the like, various excipients such as wetting agent, sweetening agent, flavoring agent, preserving agent and the like can be used, as well as simple diluents including water, liquid, paraffin and the like. The formulations for parenteral administration include sterile aqueous solution, non-aqueous solvent, suspending agent, emulsifying agent, freeze-drying agent, suppository and transdermal agent. The suspending agent and non-aqueous solvent include propylene glycol, polyethylene glycol, plant oil such as olive oil, injectable ester such as ethyl oleate, and the like. The base material for suppository can be witepsol, macrogol, tween 61, cacao oil, laurin oil, glycerol gelatin and the like.

The pharmaceutical composition of the present invention can be administered to a human alone, or in combination of pharmaceutically-acceptable diluents which are selected on the basis of the administration route and standard pharmaceutical practice. For examples, the composition can be formulated as a tablet containing starch or lactose, a capsule containing an active ingredient alone or in combination of excipient, an elixir or suspension including a flavoring agent or a coloring agent, to be administered orally, intra-orally, or sublingually. The liquid solution can be formulated together with pharmaceutically-acceptable additives such as a suspending agent (for examples, semi-synthetic glyceride including methyl cellulose and witepsol, a mixture of apricot kernel oil or PEG-6 ester, or a mixture of glyceride including PEG-8 and caprylic/capric glyceride).

The usage of pharmaceutical composition can be adjusted by considering the age, body weight, gender, administering mode, condition and severity of the subject and the like. According to the determination of doctor or pharmacist, the composition can be administered one to several times in a day at constant interval. For example, based on the content of active ingredient, the daily amount of composition can be 0.5 to 50 mg/kg, and preferably 1 to 30 mg/kg. The dosage is provided as an average case, but can be higher or lower dosage being dependent on the subject. When the daily dosage of composition is less than the range, it is difficult to reach the proper efficacy. When it exceeds the range, it is not economical and causes a side-effect.

The food composition of the present invention, food refers to natural or artificial product containing at least one nutrient, and generally includes various foods, health functional food, beverage, food additives, and beverage additives. The food composition means a combination of the materials to be used for various foods. The examples of food include foods, beverages, gums, teas, functional food and the like. Also, the food for special nutrient food such as milk formulas and infant/baby food, processed meat product, processed fish product, tofu, gellied food, noodles such as ramen and noodle, health supplement food, snacks, other processed food, beverage, health functional beverage such as a food for relieving hangovers, and other dietary supplements, but not limited thereto. The health functional food, beverage, food additive or beverage additive can be prepared according to the convention method to make them.

In another embodiment, there is provided a method of preparing Justicidin A, 5-methoxyjusticidin A or Chinensinaphthol from the *Monsonia* sp. plant.

The method comprises the steps of: extracting a plant of *Monsonia* sp. with at least one solvent selected from the group consisting of water, $C_1$ to $C_4$ linear or branched alcohol, ethyl acetate, dichloromethane and acetone; and performing column chromatography with elution solution of mixed hexane and ethyl acetate at a mixing ratio of 7:3 to 9.5:0.5 (v/v) (hexane:ethyl acetate).

The *Monsonia* sp. plant can be *Monsonia angustifolia*.

The extracting solvent selected from the group consisting of water, $C_1$ to $C_4$ linear or branched alcohol, ethyl acetate, dichloromethane and acetone can be preferably used at an amount of 1 or 5 times as the volume of *Monsonia* sp. plant to be used. The extracting time can be preferably 1 to 12 hour, most preferably 2 to 5 hour, but is not limited thereto. The extracting step can be performed at least two times, and remnant obtained in previous extracting step can be further extracted repetitively and then mixed with the filtered solution.

The column chromatograph can be performed by using silica gel, but is not limited thereto.

As described above, the composition including Justicidin A, 5-methoxyJusticidin A, and/or Chinensinaphthol as an active ingredient effectively inhibits the formation of beta-amyloid (A$\beta$40, A$\beta$42) which has been known as a causing factor of dementia, particularly Alzheimer's disease, and thus can be used for preventing or treating dementia and for ameliorating the memory impairment and improving memory.

EXAMPLES

The present invention will be further described by referring to examples. However, these examples should not be interpreted as limiting the scope of the invention in any manner.

Example 1

Preparation for an Extract of *Monsonia angustifolia*

*Monsonia angustifolia* grown naturally in Pretoria of South Africa was collected on January to February, 2010 and used for the test. Reference sample of No. 39250002 is preserved at herbarium of South African National Biodiversity Institute.

Whole plant of *Monsonia angustifolia* was finely cut and 266 g cut plant material was put into an extractor. In the extractor, 6 L of a mixed solvent of methanol and dichloromethane at mixing ratio of 1:1 (v/v) was added to, extracted for 1 hour at a room temperature with stirring and then filtered. The residue was added with 3 L of a mixed solvent of methanol and dichloromethane at mixing ratio of 1:1 (v/v), extracted secondly for 1 hour, and filtered to obtain a filtered solution. The solution was mixed with primary-filtered solution. After filtering the mixture, the produced solution was concentrated in a concentrator under a reduced pressure at 40° C., until the solvent was completely removed, to obtain 27.3 g extract of *Monsonia angustifolia* (S62) (Yield: 10.3%).

Example 2

Separation and Identification of Compounds 6 g of *Monsonia angustifolia* extract obtained in Example 1 was carried out with silica gel column chromatograph (silica gel 60, Merck, 230-400 mesh) using a mixture of hexane and ethyl acetate at a ratio of 8.5:1.5 (v/v) as an elution solution to obtain the compounds contained in the extract. As a result, 19.3 mg of Justicidin A white powder (yield 0.3%), 35 mg of 5-methoxyJusticidin A white powder (yield 0.6%), 27 mg of Chinensinaphthol white powder (yield 0.45%), 16 mg of retrochinensinaphthol methylether (yield 0.26%) and 36 mg of succilactone yellow crystalline form (0.6%) were obtained from 6 g of *Monsonia angustifolia* extract.

The structures of compounds were analyzed with NMR analysis and mass analysis.

Specifically, to identify the molecular weight and structure, as a result of measurement of mass spectrum using Agilent 1100 HPLC-ESI-MS), $[M+1]^+$ peak of m/z 395 was observed and thus the molecular weight of Justicidin A was determined as 394. In comparison of NMR spectrum with NMR machine (Varian 500 MHz NMR) with the known references (Okigawa et al, Tetrahedron, 1970, 26, 4301; Badheka et al, Phytochemistry, 1986, 25, 487), the structure was represented by Chemical Formula 1 and determined as Justicidin A:

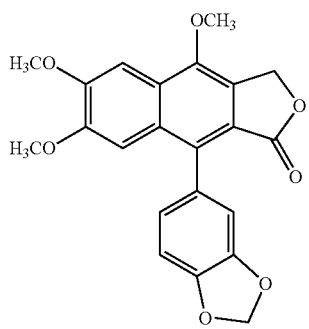

<Chemical Formula 1>

White powder; $C_{22}H_{18}O_7$; ESI-MS: m/z 395 $[M+1]^+$

TABLE 1

The NMR analysis result of Justicidin A (in CDCl₃)

| C | $\delta_C$ | Dept & HMQC | $\delta_H$ ($J_{HH}$ in Hz) | HMBC $^{>1}J_{CH}$ correlations |
|---|---|---|---|---|
| 1 | 169.5 | C=O | | |
| 3 | 66.6 | CH₂ | 5.51 | C-9a, C-4, C-1 |
| 3a | 119.3 | C | | |
| 4 | 147.8 | C | | |
| 4a | 126.0 | C | | |
| 5 | 100.6 | C | 7.52 | |
| 6 | 151.6 | C | | |
| 7 | 150.4 | C | | |
| 8 | 106.2 | CH | 7.04 | C-4a, C-9, C-6 |
| 8a | 130.7 | C | | |
| 9 | 134.4 | C | | |
| 9a | 124.5 | C | | |
| 4-OCH₃ | 59.7 | OCH₃ | 4.11 | C-4 |
| 6-OCH₃ | 56.1 | OCH₃ | 4.04 | C-6 |
| 7-OCH₃ | 55.8 | OCH₃ | 3.79 | C-7 |
| 2' | 101.2 | CH₂ | 6.02, 6.06 (d, 1.0) | C-7a', C-3a' |
| 3a' | 147.5 | C | | |
| 4' | 110.8 | CH | 6.8 (s) | C-6', C-9, C-7a' |
| 5' | 128.5 | C | | |
| 6' | 123.6 | CH | 6.76, 6.78 (dd, 7.9, 1.4) | C-4', C-9, C-7a' |
| 7' | 108.2 | CH | 6.92, 6.94 (d, 7.9) | C-5', C-3a' |
| 7a' | 147.4 | C | | |

¹³C NMR (125 MHz, CDCl₃) and ¹H NMR (500 MHz, CDCl₃)

By measuring the molecular weight of 5-methoxyJusticidin A with HPLC-MS, its molecular weight was 424. In comparison of NMR spectrum with NMR machine (Varian 500 MHz NMR) with the known references (Siani et. al., J. Nat. Prod. 1998, 795), the structure was represented by Chemical Formula 2 and determined as 5-methoxyJusticidin A:

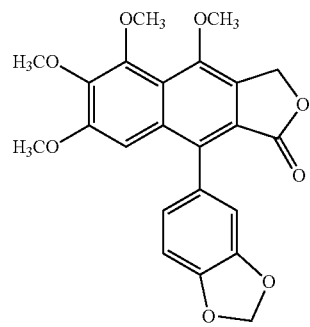

<Chemical Formula 2>

White powder; $C_{23}H_{20}O_8$; ESI-MS: m/z 425 $[M+1]^+$

TABLE 2

The NMR analysis result of 5-methoxyJusticidin A (in CDCl₃)

| C | $\delta_C$ | $\delta_H$ (J in Hz) | HMBC $^{>1}J_{CH}$ correlations |
|---|---|---|---|
| 1 | 169.5 | | |
| 3 | 66.5 | 5.41 (s) | C-1, C-4, C-9a |
| 3a | 120.7 | | |
| 4 | 149.1 | | |
| 4a | 122.2 | | |
| 5 | 148.1 | | |
| 6 | 144.9 | | |
| 7 | 153.1 | | |
| 8 | 103.7 | 6.94(s) | C-4a, C-6, C-9 |
| 8a | 133.5 | | |
| 9 | 135.6 | | |
| 9a | 129.9 | | |
| 4-OCH₃ | 62.0 | 3.97(s) | C-4 |
| 5-OCH₃ | 62.4 | 3.95(s) | C-5 |
| 6-OCH₃ | 61.4 | 4.01(s) | C-6 |
| 7-OCH₃ | 55.8 | 3.74(s) | C-7 |
| 2' | 101.2 | 6.02, 6.07 (d, 1.4; d, 1.4) | C-7a', C-3a' |
| 3a' | 147.6 | | |
| 4' | 110.6 | 6.78 (d, 1.3) | C-6', C-9, C-7a' |
| 5' | 128.5 | | |
| 6' | 123.6 | 6.75, 6.76 (dd, 1.6, 7.9) | C-4', C-9, C-7a' |
| 7' | 108.3 | 6.92, 6.94 (d, 7.9) | C-5', C-3a' |
| 7a' | 147.5 | | |

¹³C NMR (125 MHz, CDCl₃) and ¹H NMR (500 MHz, CDCl₃)

By measuring the molecular weight of Chinensinaphthol with HPLC-MS, its molecular weight was 380. In comparison of NMR spectrum with NMR machine (Varian 500 MHz NMR) with the known references (Chang et. al., Phytochemistry 2003, 64, 1375; Yang et. al., Magnetic Resonance in Chemistry 2006, 44, 727), the structure was represented by Chemical Formula 3 and determined as Chinensinaphthol:

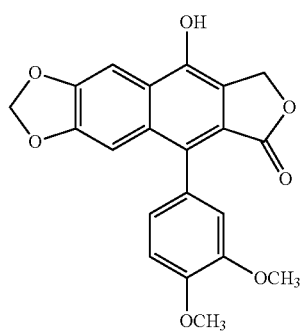

<Chemical Formula 3>

White powder; $C_{21}H_{16}O_7$; ESI-MS: m/z 381 [M+1]$^+$

TABLE 3

The NMR analysis result of Chinensinaphthol
(in mixed solution of $CDCl_3$ and $CD_3OD$)

| C | $\delta_C$ | Dept & HMQC | $\delta_H$ (J in Hz) | COSY | HMBC $^{>1}J_{CH}$ correlations |
|---|---|---|---|---|---|
| 1 | 169.4 | C=O | | | |
| 3 | 66.4 | $CH_2$ | 5.35 (s) | | C-1, C-9a, C-4 |
| 3a | 119.0 | C | | | |
| 4(—OH) | 145.1 | C | | | |
| 4a | 124.6 | C | | | |
| 5 | 97.9 | CH | 7.61 (s) | | C-8a, C-4, C-7 |
| 6 | 148.6 | C | | | |
| 7 | 148.0 | C | | | |
| 8 | 102.5 | CH | 6.85 (s) | | C-4a, C-6, C-9 |
| 8a | 131.0 | C | | | |
| 9 | 130.3 | C | | | |
| 9a | 122.3 | C | | | |
| 10 | 101.9 | $CH_2$ | 6.15 (s) | | C-6, C-7 |
| 1' | 127.5 | C | | | |
| 2' | 114.2 | CH | 6.83 (d, 2.1) | H-6' | C-4', C-6', C-9 |
| 3' | 148.2 | C | | | |
| 4' | 148.3 | C | | | |
| 5' | 111.2 | CH | 7.05 (d, 8.2) | H-6' | C-1', C-3' |
| 6' | 122.5 | CH | 6.77 (dd, 2.1, 8.0) | H-5', H-2' | C-2', C-3', C-9 |
| 3'-$OCH_3$ | 55.5 | $OCH_3$ | 3.71 (s) | | C-3' |
| 4'-$OCH_3$ | 55.4 | $OCH_3$ | 3.84 (s) | | C-4' |

* $^{13}$C NMR (100 MHz) and $^1$H NMR (400 MHz)

By measuring the molecular weight of Retrochinensinaphthol methylether with HPLC-MS, its molecular weight was 394. In comparison of NMR spectrum with NMR machine (Varian 400 MHz NMR) with the known references (Chang et al, Phytochemistry 2003, 64, 1375; Yang et al, Magnetic Resonance in Chemistry 2006, 44, 727), the structure was represented by Chemical Formula 4 and determined as Retrochinensinaphthol methylether:

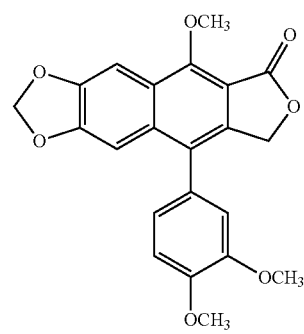

<Chemical Formula 4>

White powder; $C_{22}H_{18}O_7$; ESI-MS: m/z 395 [M+1]$^+$

TABLE 4

The NMR analysis result of Retrochinensinaphthol
methylether (in $CDCl_3$)

| C | $\delta_C$ | Dept & HMQC | $\delta_H$ (J in Hz) | COSY | HMBC $^{>1}J_{CH}$ correlations |
|---|---|---|---|---|---|
| 1 | 169.1 | C=O | | | |
| 3 | 68.8 | $CH_2$ | 5.11 (d, 15.0; d, 15.0) | | C-1, C-4, C-9a |
| 3a | 139.4 | C | | | |
| 4 | 127.5 | C | | | |
| 4a | 135.3 | C | | | |
| 5 | 102.2 | CH | 6.98 (s) | H-8 | C-7, C-8a, C-4 |
| 6 | 148.2 | C | | | |
| 7 | 150.8 | C | | | |
| 8 | 100.2 | CH | 7.71 (s) | | C-4a, C-6, C-9 |
| 8a | 125.3 | C | | | |
| 9 | 155.7 | C | | | |
| 9a | 110.1 | C | | | |
| 10 | 101.8 | $CH_2$ | 6.06 (s) | | C-6, C-7 |
| 9-$OCH_3$ | 63.5 | $OCH_3$ | 4.31 (s) | | C-9 |
| 1' | 128.5 | C | | | |
| 2' | 112.6 | CH | 6.79 (d, 2.0) | H-6' | C-4', C-6', C-4 |
| 3' | 149.4 | C | | | |
| 4' | 149.0 | C | | | |
| 5' | 111.8 | CH | 6.99 (d, 8.0) | H-6' | C-1', C-3' |
| 6' | 121.9 | CH | 6.84, 6.86 (dd, 2.0, 8.0) | H-5', H-2' | C-2', C-4', C-4 |
| 3'-$OCH_3$ | 56.1 | $OCH_3$ | 3.86 (s) | | C-3' |
| 4'-$OCH_3$ | 56.0 | $OCH_3$ | 3.96 (s) | | C-4' |

* $^{13}$C NMR (100 MHz) and $^1$H NMR (400 MHz)

By measuring the molecular weight of succilactone with HPLC-MS, its molecular weight was 368. In comparison of NMR spectrum with NMR machine (Varian 400 MHz NMR) with the known references (Banerji et al, Phytochemistry 1984, 23, 2323), the structure was represented by Chemical Formula 5 and determined as succilactone:

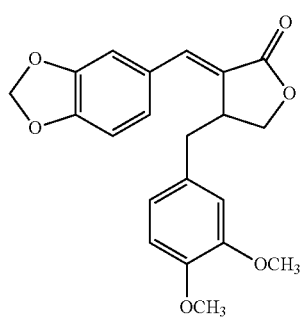

<Chemical Formula 5>

Yellow crystalline form; $C_{21}H_{20}O_6$; EI-MS: m/z 368 [M]$^+$

TABLE 5

The NMR analysis result of succilactone (in $CDCl_3$)

| C | $\delta_C$ | $\delta_H$ (J in Hz) | DEPT | COSY | HMBC $^{>1}J_{CH}$ correlations |
|---|---|---|---|---|---|
| 2 | 172.5 | | C=O | | |
| 3 | 126.1 | | C | | |
| 4 | 40.1 | 3.75 (m) | CH | H-7", H-5 | C-8', C-2, C-1" |
| 5 | 69.8 | 4.26 (m) | $CH_2$ | H-4 | C-7", C-3, C-2 |
| 2' | 101.7 | 6.02 (d, 1.9) | $CH_2$ | | C-3a', C-7a' |
| 3a' | 148.4 | | C | | |
| 4' | 126.3 | 7.08 (s) | CH | | C-6', C-7a', C-8' |
| 5' | 128.3 | | C | H-6' | |
| 6' | 108.5 | 7.06 (s) | CH | H-7', H-4' | C-4', C-8', C-7a' |
| 7' | 108.8 | 6.87 (dd, 8.5, 1.9) | CH | H-6' | C-5', C-3a' |
| 7a' | 149.2 | | C | | |
| 8' | 137.2 | 7.50 (d, 1.9) | CH | | C-4', C-6', C-2, C-4 |
| 1" | 130.4 | | C | | |
| 2" | 120.9 | 6.73 (dd, 2.0, 8.2) | CH | | C-4", C-6", C-7" |
| 3" | 149.2 | | C | | |
| 4" | 148.1 | | C | | |
| 5" | 111.5 | 6.85 (d, 8.1) | CH | H-6" | C-1", C-3" |
| 6" | 112.2 | 6.69 (d, 2.0) | CH | | C-2", C-4", C-7" |
| 7" | 37.7 | 2.63 (dd, 14.13, 4.31); 3.01 (dd 14.12, 10.02) | $CH_2$ | H-4 | C-3, C-5, C-2", C-6" |
| 4"-$OCH_3$ | 55.9 | 3.86 (s) | $OCH_3$ | | C-4" |
| 3"-$OCH_3$ | 55.9 | 3.84 (s) | $OCH_3$ | | C-3" |

* $^{13}C$ NMR (100 MHz), $^1H$ NMR (400 MHz)

Experimental Example 1

The Inhibitory Effect of Justicidin A and 5-methoxyJusticidin A on the Formation of β-Amyloid <1-1> Inhibition of Justicidin A on β-Amyloid Formation To test the inhibitory effect of Justicidin A (C1) obtained in Example 2 on the beta-amyloid formation, HeLa cell line transfected with the amyloid precursor protein (APP) driven from human was cultured in DMEM solution (Cat. #11995, Gibco, USA) for use. The cell line was received from Prof. Tae-Wan Kim at Department of Pathology, Columbia University Medical Center, New York, N.Y. 10032, USA.

Specifically, the Justicidin A of Example 2 was added into the cell line culture at the amount indicated in FIG. 1, and then the produced amount of be-amyloid (Aβ40, Aβ42 was measured. Human β-Amyloid[1-40](Aβ40), Human β-Amyloid [1-42](Aβ42) Colorimetric ELISA kit (#KHB3482 and #KHB3442; BioSource International, Inc., U.S.A.) were used to quantify two types of beta-amyloid (Aβ40, Aβ42).

Figure 1B:
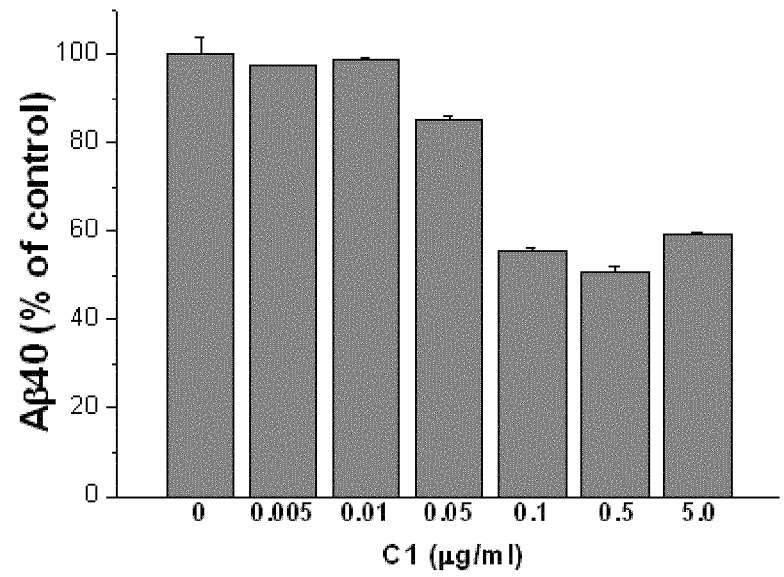

The product amounts of β-amyloid were summarized in FIGS. 1a and 1b. The group which was not treated with Justicidin A was used as a negative control. As shown in FIG. 1, the Justicidin A inhibited the beta-amyloid (Aβ40, Aβ42) formation at a concentration-dependent manner.

<1-2> Inhibition of 5-methoxyJusticidin A on β-Amyloid Formation

The 5-methoxyJusticidin A (C2) of Example 2 was added into the cell line culture at the amount indicated in FIG. 2, and then the produced amount of be-amyloid was measured according to the method of Example 1.1. The group which was not treated with 5-methoxyjusticidin A was used as a negative control.

Figure 2A:
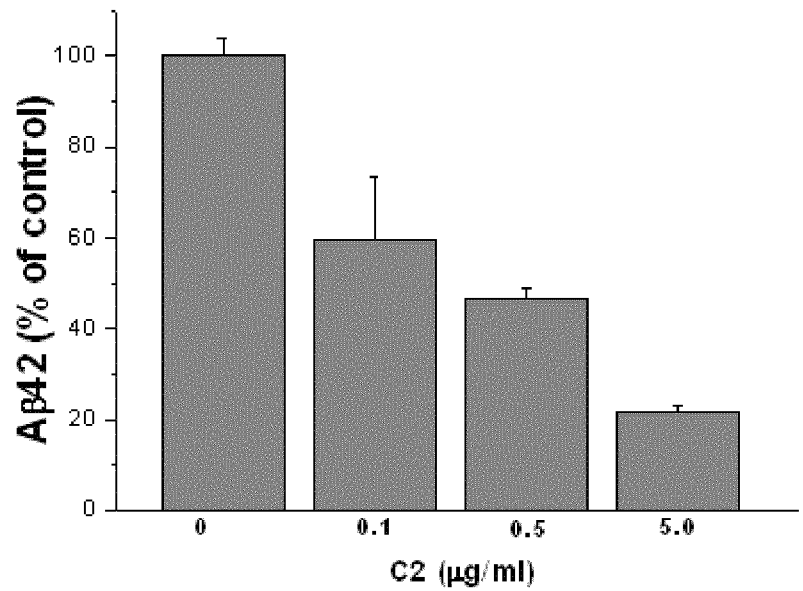
FIGS. 2a and 2b are graphs showing the inhibitory effect on the formation of beta-amyloid at various concentrations of added 5-methoxyJusticidin A (C2) obtained in Example 2 (Aβ42 in upper; Aβ40 in lower, and 0: negative control).
Figure 2B:
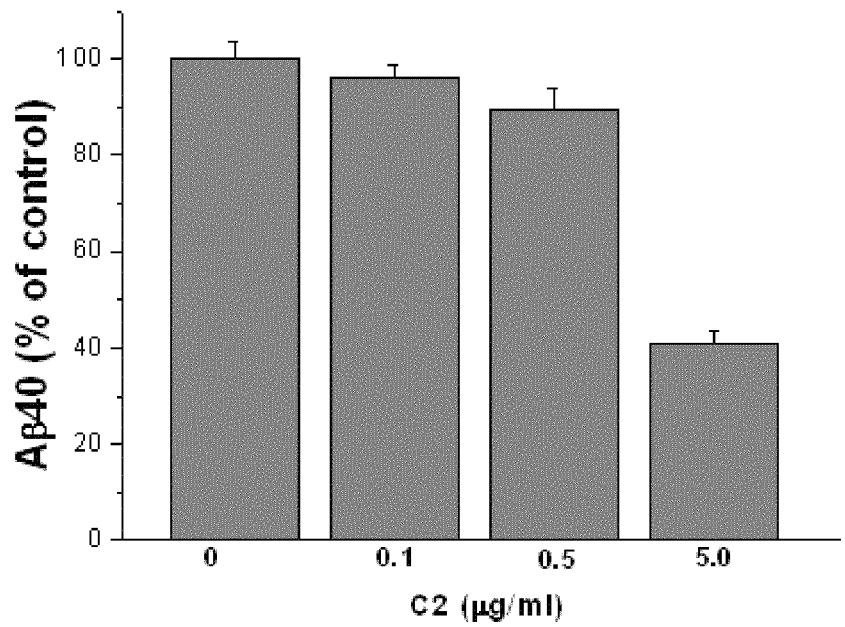

The product amounts of β-amyloid were summarized in FIGS. 2a and 2b. The group which was not treated with 5-methoxyJusticidin A was used as a negative control. As shown in FIGS. 2a and 2b, 5-methoxyJusticidin A inhibited the beta-amyloid (Aβ40, Aβ42) formation at a concentration-dependent manner.

Experimental Example 2

The Effect of Justicidin A and 5-methoxyJusticidin A on Cell Death and Safety Test To test the effect of Justicidin A and 5-methoxyJusticidin A on cell death, the MTT Cell Proliferation assay method (ATCC catalog #30-1010K, Manassas, USA) was used. Specifically, the HeLa cell line transfected with the amyloid precursor protein (APP) driven from human was treated with various concentrations of Justicidin A (S62-C1) or 5-methoxyJusticitdin A (S62-C2) for 8 hours, and the viable cells were quantified to show the result in FIG. 3.

Figure 3:
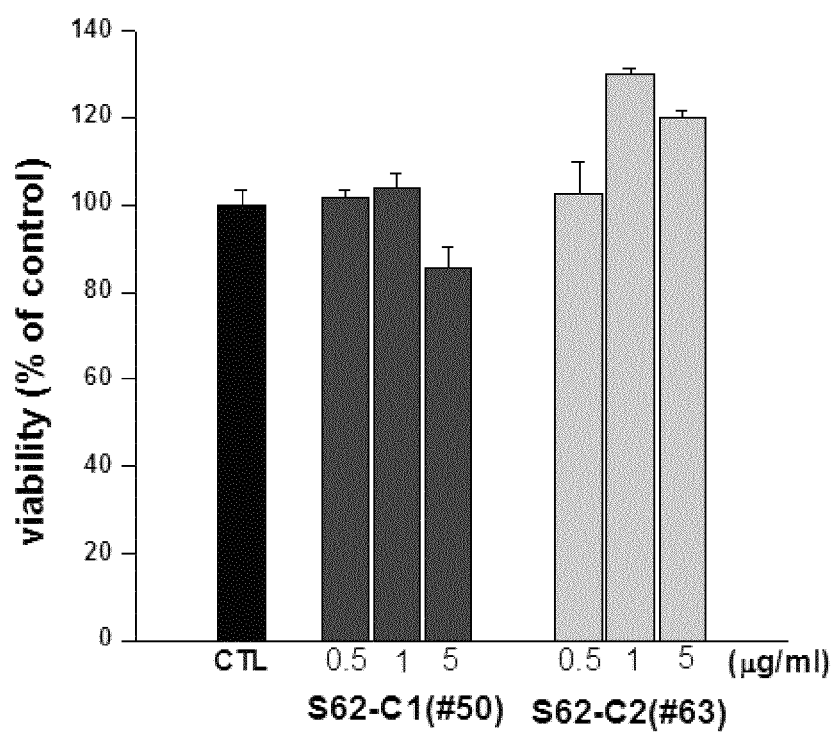
FIG. 3 is a graph showing the effect on cell death at various concentrations of added Justicidin A (S62-C1) or 5-methoxy-Justicidin A (S62-C2) (CTL: negative control).

As shown in FIG. 3, when the cell lines were treated with 5-methoxyJusticidin A (S62-C2) at a concentration of 5 μg/ml, the cell lines did not die nearly. When the cell lines were treated with 5 μg/ml of Justicidin A (S62-C1), only 20% or less of cell lines died.

Therefore, it suggested that the inhibition of the beta-amyloid (Aβ40, Aβ42) formation caused by Justicidin A and 5-methoxyJusticidin A was not simply driven by the cell death, and that Justicidin A and 5-methoxyJusticidin A could be used safely as an active ingredient in pharmaceutical or food composition in effective amount ranges to sufficiently and effectively inhibit beta-amyloid formation.

Experimental Example 3

Inhibition of Beta-Secretase Activity

This test was performed for specifically identifying the cause of inhibition of beta-amyloid formation in Experimental Example 1. The beta-amyloid is produced by sequential actions of beta-secretase (BACE1) and gamma-secretase on APP (Vassa and Citron, Neuron 27, 419-422, 2000). More specifically, APP was changed to beta-secretase product (sAPPβ) by beta-secretase, and then beta-amyloid was made by gamma-secretase. Therefore, the inhibition of beta-secretase results in the inhibition of beta-amyloid (Aβ40, Aβ42).

To confirm that the inhibition of beta-amyloid (Aβ40, Aβ42) formation caused by Justicidin A and 5-methoxyJusticidin A in Example 2 is caused by the inhibition of beta-secretase, the beta-secretase activity was measured by using HeLa cell line transfected with the amyloid precursor protein (APP) driven from human and beta-secretase fluorometric assay kit (#K360-100; Biovision, USA). 5 μM beta-secretase inhibitor (#565788; Calbiochem, USA) was used for a positive control and no treating group with Justicidin A or 5-methoxyJusticidin A was used for a negative control.

Figure 4:
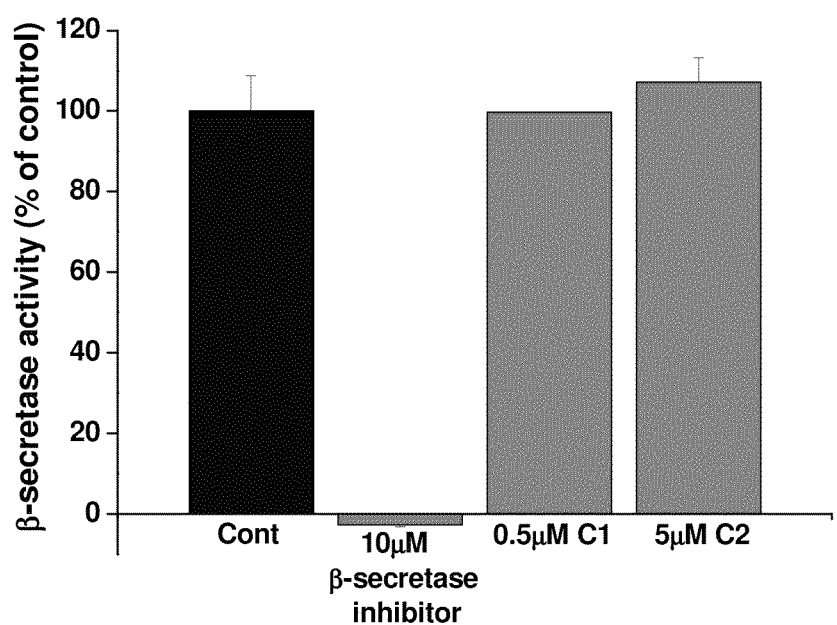
FIG. 4 is a graph showing the inhibitory effect of 0.5 μM Justicidin A or 5 μM 5-methoxyjusticidin A on beta-secretase activity (beta-secretase inhibitor: positive control, Cont: negative control).

The result was shown in FIG. 4. As shown in FIG. 4, the beta-secretase was not affected with treatment of 0.5 μM Justicidin A (S62-C1) and 5 μM 5-methoxy Justicidin A (S62-C2).

Therefore, it confirmed that the inhibition of beta-amyloid (Aβ40, Aβ42) formation by Justicidin A or 5-methoxyJusticidin A was not caused by the inhibition of beta-secretase.

Experimental Example 4

The Activation of Alpha-Secretase

This test was carried out in order to specifically identify the cause of beta-amyloid formation in Experimental Example 1, without inhibiting the beta-secretase in Experimental Example 3.

The beta-amyloid formation is inhibited by the activation of alpha-secretase also, and alpha-secretase acts against the beta-secretase in production of beta-amyloid. The beta-secretase acts largely on the formation of Aβ42 and APP-β, while the alpha-secretase acts the formation of APP-α having the neuron protection activity and has a relatively-low affect on the reduction of the beta-amyloid formation.

The test result confirmed that Justicidin A (C1) obtained in Example 2 and 5-methoxyJusticidin A increased alpha-secretase product (sAPPα). Specifically, the produced amount of sAPPα was measured by treating the cultured cell line (the HeLa cell line transfected with the amyloid precursor protein (APP) driven from human) with Justicidin A (S62-C1) or 5-methoxyJusticitdin A (S62-C2) at a concentration of FIG. 5, culturing it for 8 hours, and measuring the produced amount of sAPPα according to the Western blotting. The negative control was the group with no treatment of Justicidin A or 5-methoxyJusticidin A.

The result was shown in FIG. 5. As shown in FIG. 5, Justicidin A and 5-methoxyjusticidin A activated the formation of alpha-secretase product (sAPPα). Justicidin A and 5-methoxyJusticidin A increased the production of sAPPα having a neuron protecting activity, resulting in the inhibition of beta-amyloid formation.

Experimental Example 5

The Inhibitory Effect on the β-Amyloid Formation Caused by Arylnaphthalene Lignan Derivatives which have Similar Parent Structures to Those of Justicidin A and 5-methoxyJusticidin A This test was carried out for the inhibitory effect of Chinensinaphthol (C3) represented by Chemical Formula 3, retrochinensinaphthol methyether (C4) represented by Chemical Formula 4 and succilactone (C5) represented by Chemical Formula 5, which were obtained from *Monsonia angustifolia* extract of Example 1, and Justicidin G(J) (ChromaDex Inc. 00010550) as represented by Chemical Formula 6, Justicidin F(T) (ChromaDex Inc. 00020012) as represented by Chemical Formula 7 and Justicidin D(L) (ChromaDex Inc. 00012176) as represented by Chemical Formula 8, which are commercially available.

The compounds were used at the amount of FIG. 6, and measured for the beta-amyloid (Aβ40, Aβ42) formation according to the same method of Experimental Example <1-1>. The group treated with Justicidin A (C1) was a positive control and the group with no treatment was a negative control.

Figure 6A:
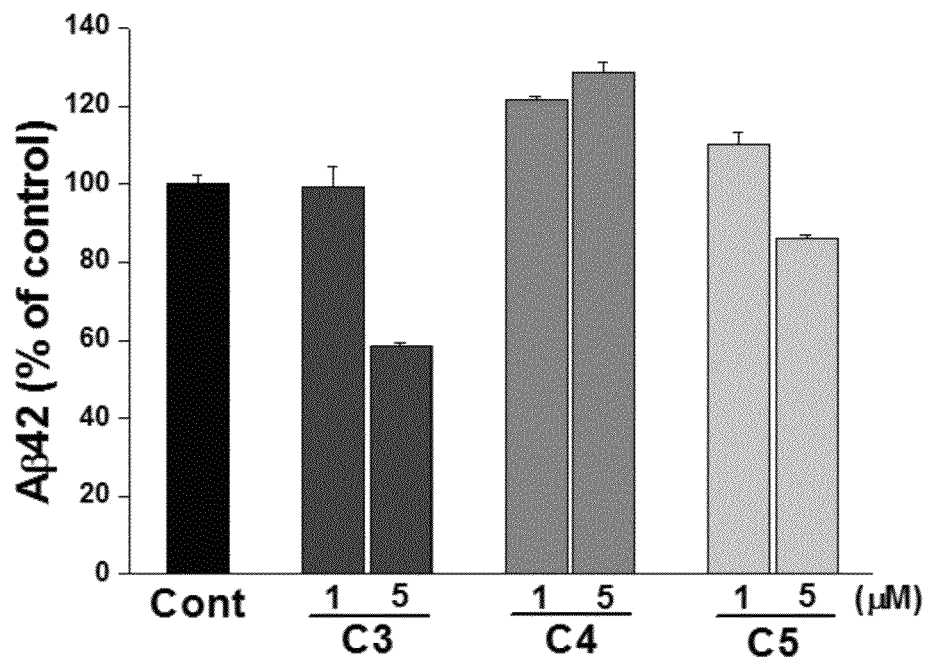
FIGS. 6a and 6b are graphs showing the inhibitory effect of Chinensinaphthol (C3), retrochinensinaphthol methyether (C4), succilactone (C5), Justicidin G(J), Justicidin F(T), Justicidin D(L) and Justicidin A (C1) on formation of Aβ42 at various concentrations (Cont: negative control).
Figure 6B:
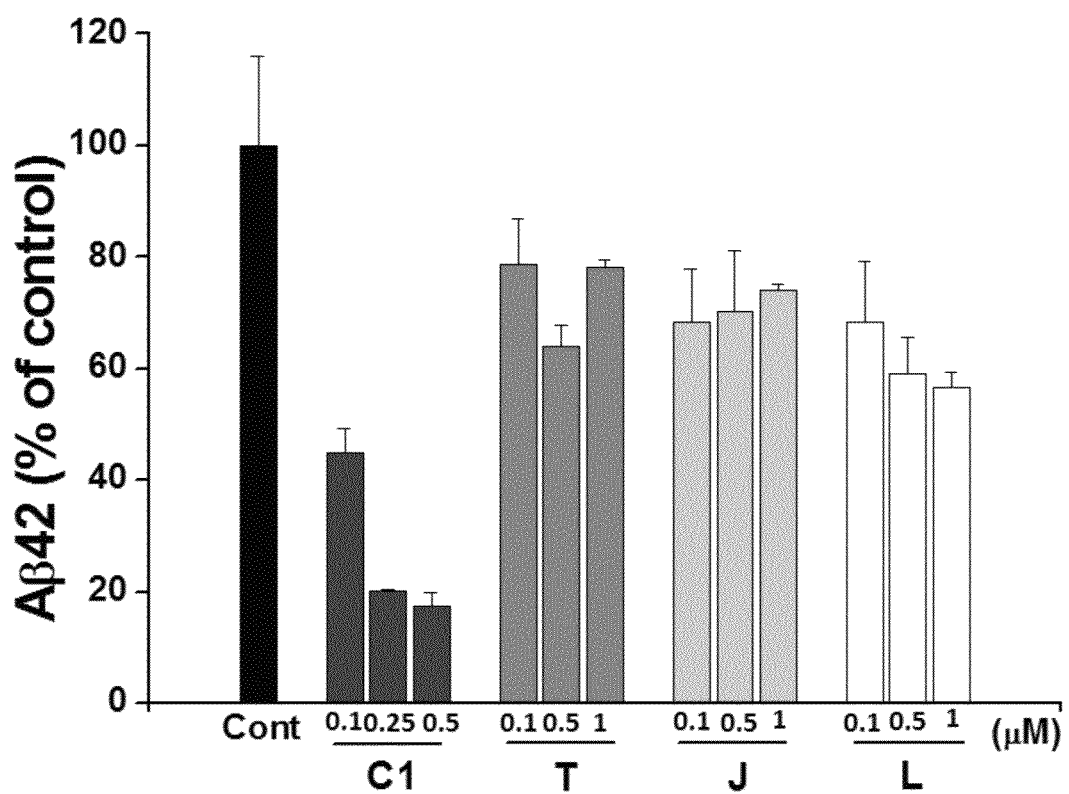

The test results were shown in FIG. 6a and FIG. 6b. The Chinensinaphthol (Chemical Formula 3) represented about 50% inhibitory effect on the beta-amyloid at 5 μg/ml. Succilactone (Chemical Formula 5) represented about 10% weak inhibitory effect on the beta-amyloid at 5 μg/ml, Justicidin G(J) (Chemical Formula 6), Justicidin F(Chemical Formula 7), and Justicidin D (Chemical Formula 8) showed about 20% inhibitory effect on the beta-amyloid at 1 μM. However, retrochinensinaphthol methyether (Chemical Formula 4) and succilactone (Chemical Formula 5) did not show nearly the inhibition of the beta-amyloid (Aβ40, Aβ42) formation.

Experimental Example 6

The Effect of Justicidin A on the Increased Targeting of Mature APP to Plasma Membrane This test was carried out in order to identify the cause of increasing of alpha-secretase product (sAPPα) in Experimental Example 4.

It is reported that APP made in ER, then passed through Golgi, targeted to plasma membrane, in the maAPP form. APP hydrolysis was performed by alpha-secretase, sAPPα secretion was increased, and Aβ secretion, made by beta secretase, was decreased. Relative amount of maAPP increased by Justicidin A, amount of APP targeted to plasma membrane was measured by biotinylation method.

Hela cell line, transfected with the amyloid precursor protein (APP), was incubated in DMEM (Cat. #11995, Gibco, USA). The cell line was received from Prof. Tae-Wan Kim at Department of Pathology, Columbia University Medical Center, New York, N.Y. 10032, USA. $1.5 \times 10^6$ cells seeded in 60 mm dish, incubated for 24 hours. Biotin group (0.25 mg/ml, 4° C., 10 min) interacted to all exposed protein of outside of cell with sulfo-NHS-SS Biotin (#21441, Thermo), then centrifuged at 16,000 g for 2 min, obtained pellet which included plasma membrane. Avidin (S 1638, Sigma), specifically interacted to biotin, added to pellet (30 ul, 4° C., incubated for 30 min) for precipitation biotinylated protein, and precipitated protein was performed electrophoresis, then measured change of APP protein, exposed protein of outside of cell, by western blotting with APP antibody (1:2000 diluted, A8717, Sigma).

The results were shown in FIGS. 7a to 7d.

Figure 7A:
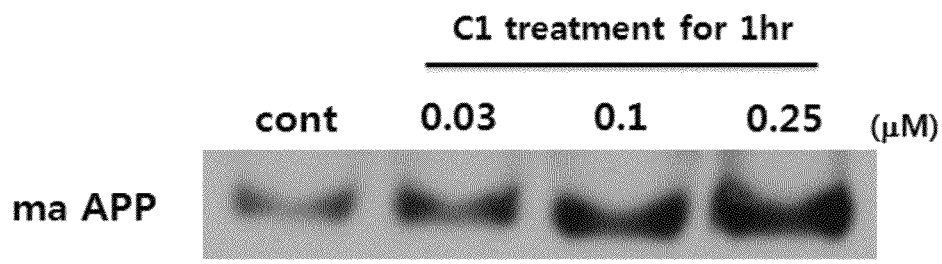
FIG. 7a to 7d show a graph and a western blotting result increasing relative amount of maAPP by Justicidin A, depending on concentration and time.
Figure 7B:
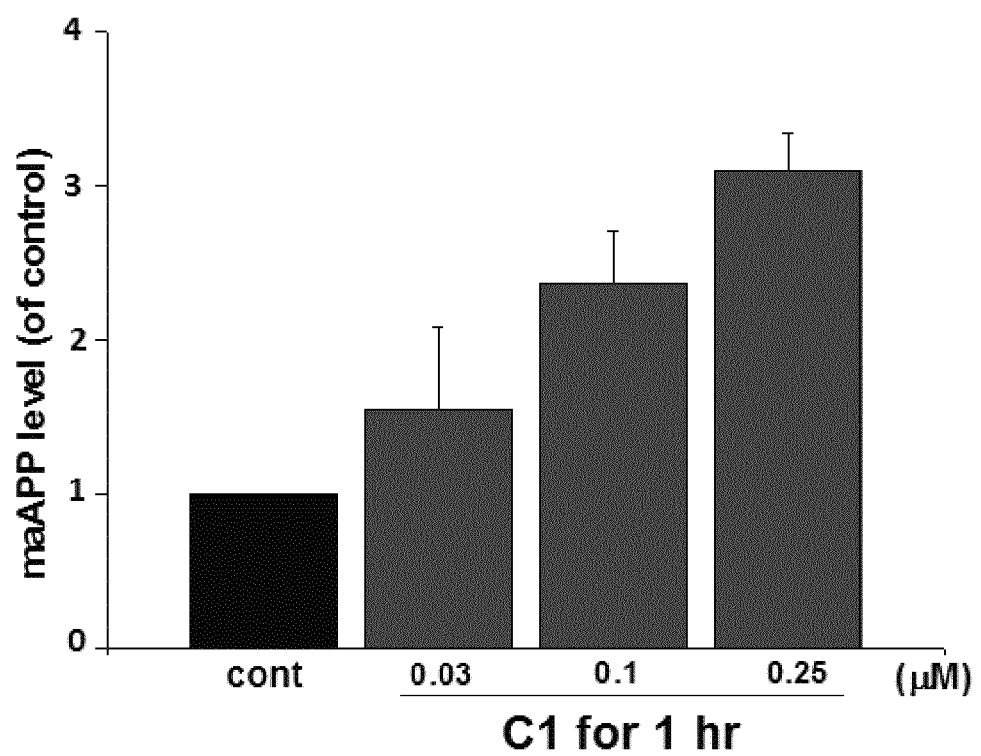
Figure 7C:
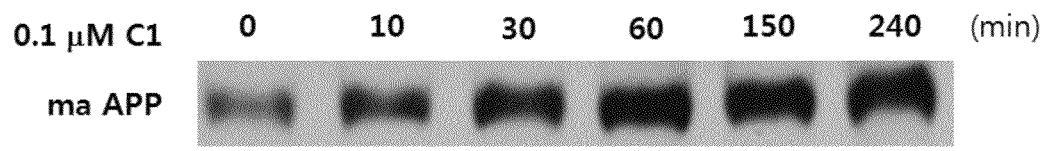
Figure 7D:
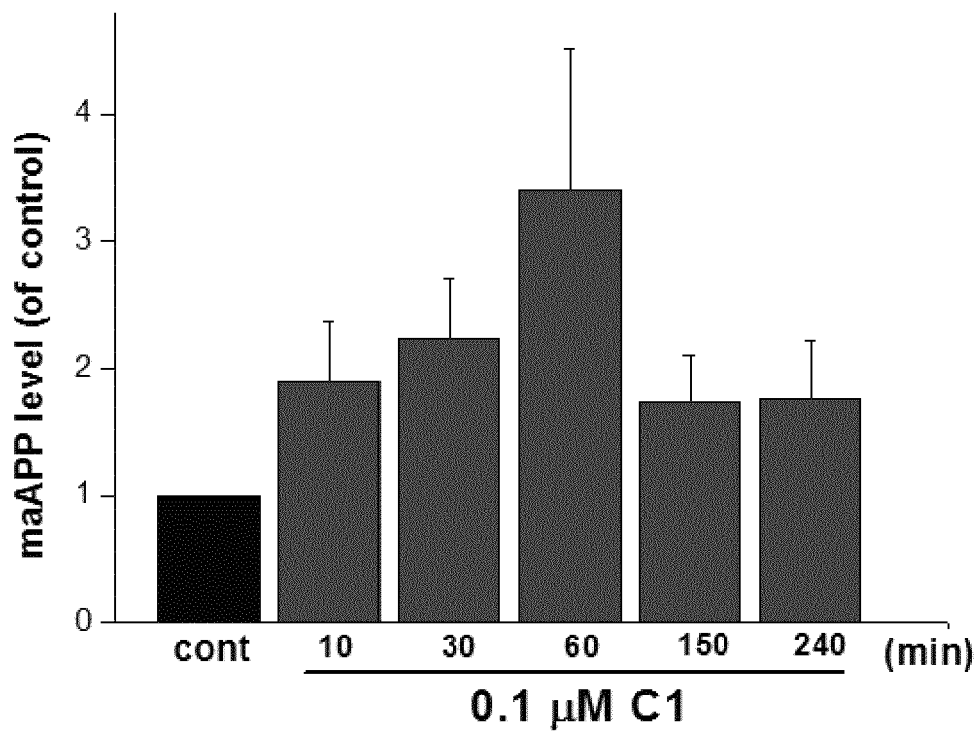

When Justicidin A was treated for 1 hour, the biotinylated APP was increased as the concentration increased 0.03, 0.1, and 0.25 uM, the and the molecular weight was the same as O-glycosylated APP (maAPP) (FIG. 7a). The result of western blotting was measured by band intensity to show the result in FIG. 7b. This result confirms that APP is targeted to plasma membrane in the form of maAPP, and the amount of maAPP increased in plasma membrane in a concentration-dependent manner. The cells were treated by the same concentration of Justicidin A (0.1 uM) by extending the treatment time from 10 min to 240 min. As a result, the amount of maAPP in the cell membrane as the treatment time increased (FIG. 7c). The result of western blotting was measured by band intensity to show the result in FIG. 7d.

Experimental Example 7

The Effect of Justicidin A on the APP O-Glycosylation

This test was carried out in order to identify the selectivity of O-glycosylation with regard to the increased formation of sAAPα caused by O-glycosylation.

The kind of protein modified by O-glycosylation was reported 200 or more proteins other than APP. To identify whether the increased O-glycosylation caused by Justicidin A is specific to APP, the antibody (#MMS-248R, Covance) recognizing all O-glycosylated proteins were used in this test. HeLa cell line which was transfected with the amyloid precursor protein (APP) as same as Experimental Example 6, $1.5 \times 10^6$ cells seeded in 60 mm dish, and incubated for 24 hours. To identify the change in O-glycosylation level by Justicidin A, the cells were treated by Justicidin A at 1, 5, and 10 uM for 4 hrs, and then centrifuged at 12,000 g for 10 min to separate the plasma membrane separated from the cell. The separated cell membrane was performed electrophoresis and western blotting with O-glycosylation antibody (1:2000 diluted, #MMS-248R, Covance).

Figure 8A:
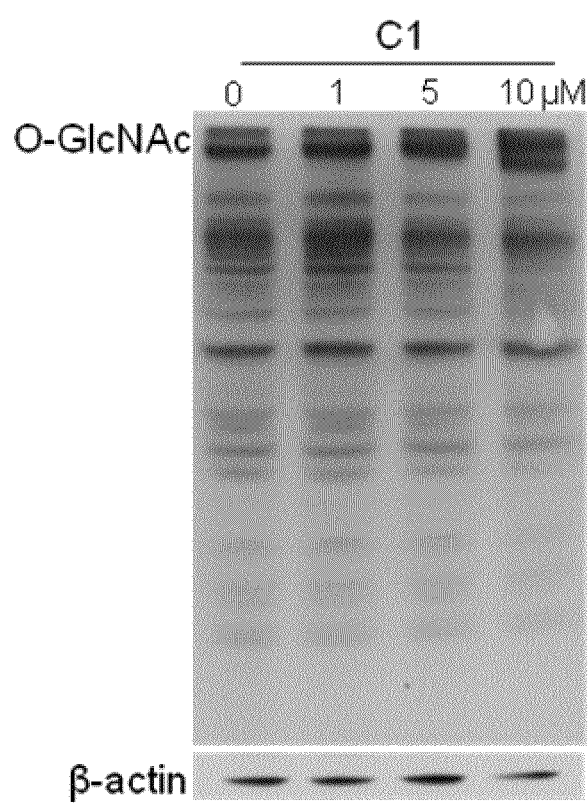
FIG. 8a to 8c show increasing of O-glycosylation by Justicidin A, which occurs to APP selectively.

The result was shown in FIG. 8a. As shown in FIG. 8a, Justicidin A was not effective to O-glycosylated protein level. The same amount of protein samples were used, which was confirmed by beta-actin. Justicidin A did not affect the whole O-glycosylation level of all proteins modified by O-glycosylation.

According to the same method as above, HeLa cell line was treated with 1, 5, 10 uM of Justicidin A for 4 hrs. Then, the 5 ul of O-glycosylation antibody (#MMS-248R, Covance) was added to 500 ug of the separated plasma membrane protein, and performed by electrophoresis and the western blotting using the APP antibody (1:2000 diluted, A8717, Sigma).

Figure 8B:
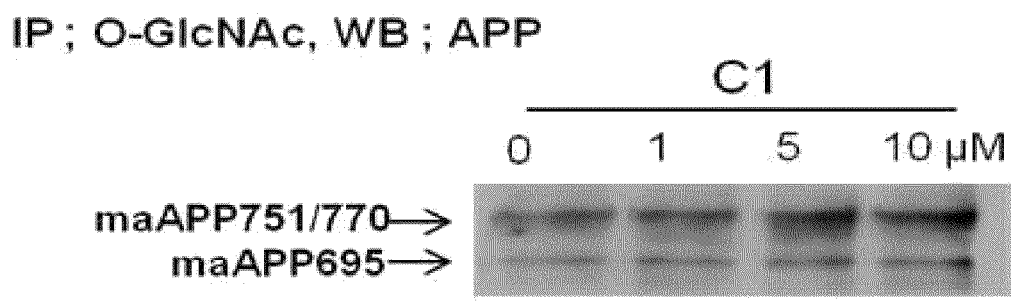

The result was shown in FIG. 8b. As shown in FIG. 8b, the O-glycosylated maAPP was increased. The O-glycosylation level of APP751/APP770 and APP695 which were isoforms of APP inside of cell, was increased.

Figure 8C:
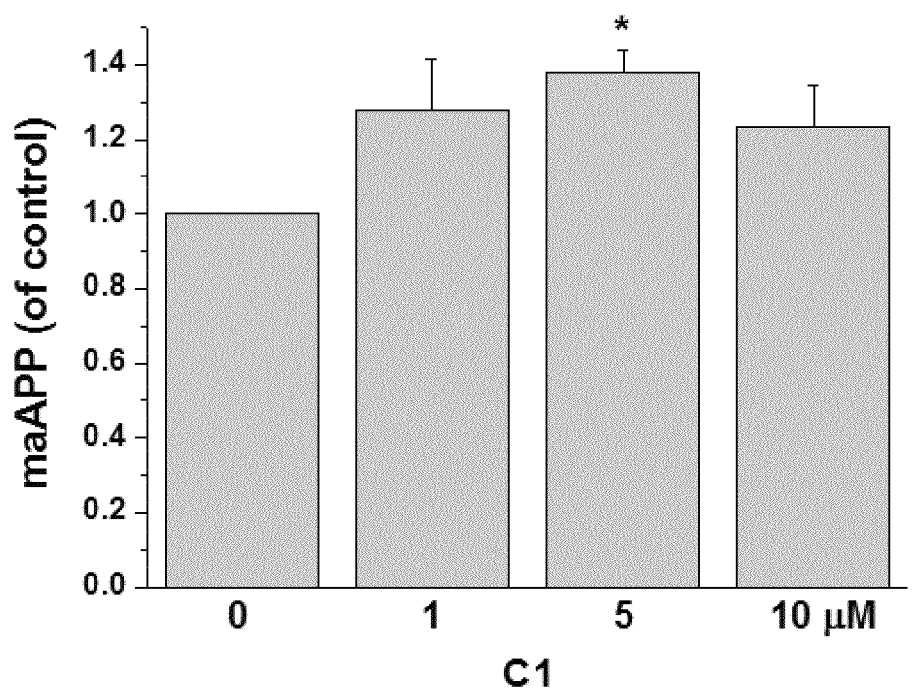

The result of western blotting was measured by band intensity to show the result in FIG. 8c. As shown in FIG. 8c, the increased APP O-glycosylation by Justicidin A was very selective to APP.

Experimental Example 8

The Effect of Justicidin A Reducing Endocytosis Rate of APP

This test was carried out in order to identify the cause of increasing of maAPP on the surface of plasma membrane by APP specific O-glycosylation in Experimental Examples 6 and 7.

One cause of increased maAPP level on plasma membrane induced by O-glycosylation is the reduced endocytosis rate of APP from cell membrane into the cell. APP endocytosis proceeded rapidly, and the reduced endocytosis rate of APP means increased maAPP level in plasma membrane. Thus, the endocytosis rate can be measured by the increased maAPP level in plasma membrane. It was reported that the increased Aβ formation was caused by increased App endocytosis (Yoon et al., Neuron, 75: 824-837, 2012). One cause of reduced Aβ is reduced endocytosis rate of APP, which is caused by Justicidin A.

To test the endocytosis rate of App, $5 \times 10^5$ cells of HeLa cell line transfected with amyloid precursor protein (APP) as the substantially same method as Experimental Examples 6 and 7, seeded on poly-D-lysine coated cover glass and incubated for 24 hours. Then, 1 uM Justicidin A and APP antibody (1:100 diluted, SIG-39320, Covance) treated for 45 min at 4° C., washed out to remove free APP antibodies with culture fluid at three times. The cells were incubated at 37° C., starting endocytosis temperature, for 10, 30, and 60 min, and fixed by 4% paraformaldehyde for 15 min. Then, the cells were permeabilized by 0.1% triton X-100 for 5 min, and APP was marked by secondary fluorescent-labeled antibody (1:200 diluted, A11001, Invitrogen).

Figure 9A:
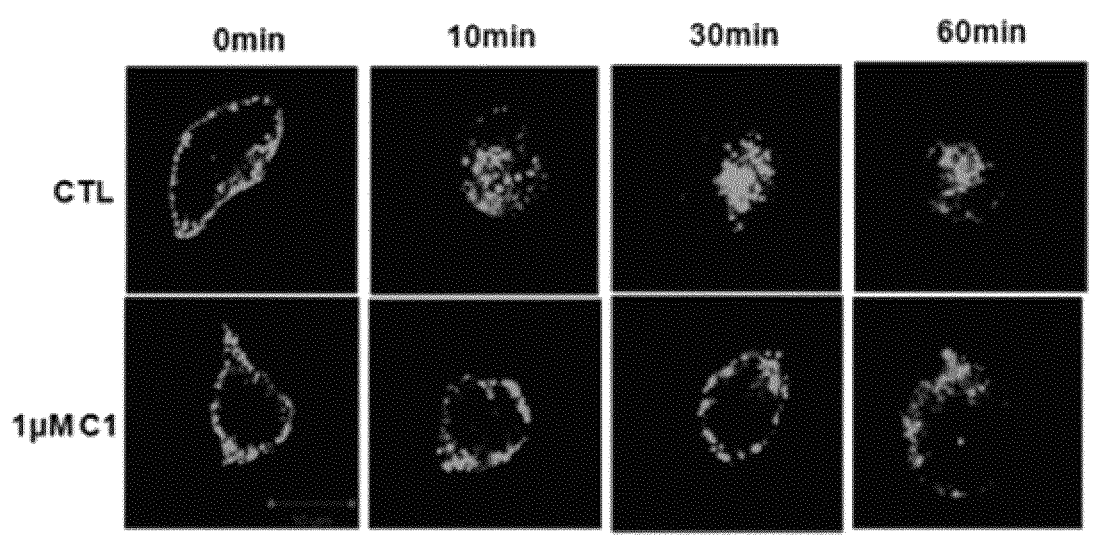
FIGS. 9a and 9b show a picture and a graph showing of endocytosis rate of APP and which is selective result by O-glycosylation of APP.

The change in the location of APP at various times was measured by confocal microscopy (LSM510, Zeiss, Germany) at 488 nm. The test results were shown in FIG. 9a. APP labeled by fluorescent antibody in plasma membrane did not start the endocytosis at 4° C. (0 min). The endocytosis started at 37° C. After 10 min, APP translocated to inside of cell from plasma membrane in control cells which were not treated Justicidin A. Also, most of APP translocated to inside of cell after 30 and 60 min. However, APP remained on plasma membrane after 10 and 30 min in the cells treated with Justicidin A.

Figure 9B:
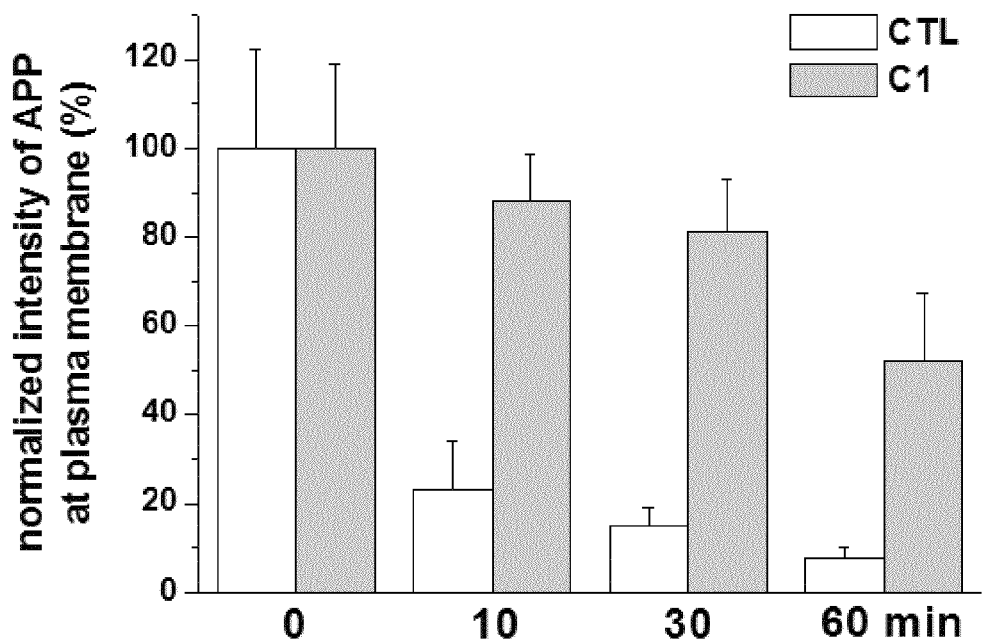

APP fluorescent intensity remained in plasma membrane compared to APP fluorescent intensity in plasma membrane at 0 min was measured. The result was shown in FIG. 9b. As shown in FIG. 9b, APP endocytosis was delayed by Justicidin A pre-treatment, so APP increased plasma membrane selectively.

For quantitative measurement of APP endocytosis rate, a reversible biotinylation method was used. $5 \times 10^5$ cells of HeLa cell line transfected with amyloid precursor protein (APP) as the same method as above, seeded 60 mm dish and added 0.25 mg/ml biotin (#21441, Thermo) and incubated 10 min, then 1 uM Justicidin A treated for 34 min. For internalization of biotinylated APP, incubated at 37° C. for 5, 10, 30 min. Reducing agent (150 mM NaCl, 1 mM EDTA, 0.2% BSA, 20 mM Tris-HCl, pH 8.6) including 50 mM sodium-2-mercapoethanesulfomate (63705, Sigma) was treated outside of cell, biotin was removed from cell surface and obtained cell lysate. Avidin (S1638, Sigma), specifically interacted to biotin, added to biotinylated protein (30 ul, 4° C., incubated for 30 min) for precipitation, separated biotin-labelled protein, endocytosis to inside of cell for a certain period time.

Figure 10A:
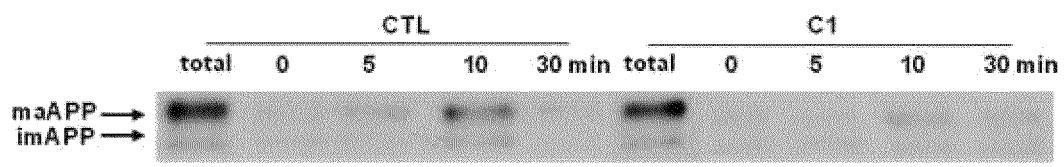
FIGS. 10a and 10b show a result of reversible biotinylation test, slowing of endocytosis rate of APP by Justicidin A, which is selective result by O-glycosylation of APP.

This protein was performed by electrophoresis, and the amount of endocytosis APP protein depending on the time, by western blotting with APP antibody (1:2000 diluted, A8717, Sigma). The results were shown in FIG. 10a. As shown in FIG. 10a, the control cell which was not treated Justicidin A showed fast endocytosis of APP after 10 min, and intracellular maAPP was increased. However, 1 uM Justicidin A pre-treated cell showed reduced endocytosis of APP, which is the same result as FIG. 9a.

Figure 10B:
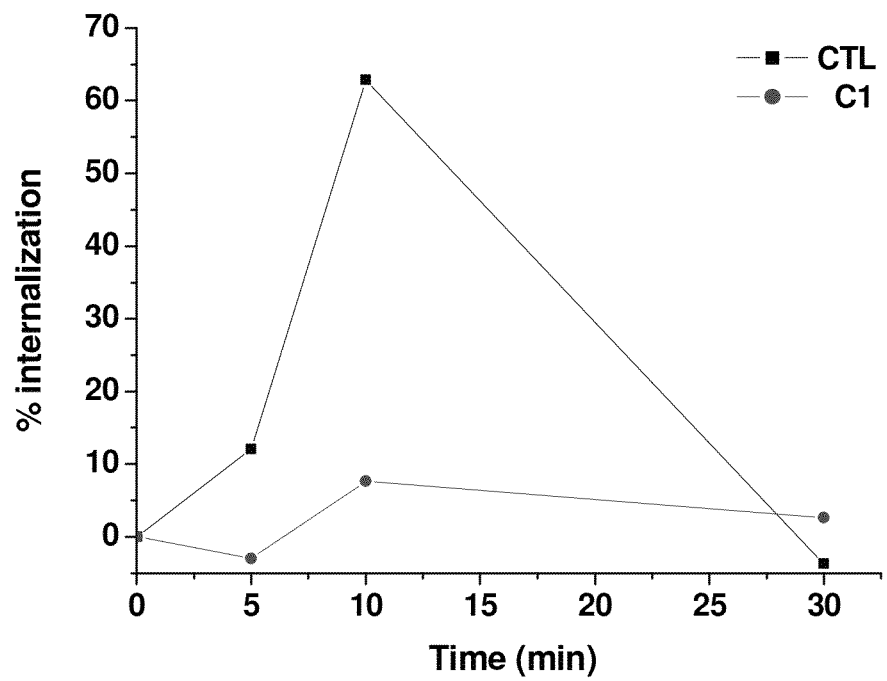

The result of western blotting was measured by band intensity to show the amount of intracellular APP (FIG. 10b; % internalization) with respect to total maAPP on the cell membrane (FIG. 10a). The result is shown in FIG. 10b.

The reduced endocytosis rate may be caused by total reduction of endocytosis other than the specific reduction of APP endocytosis rate, because many proteins other than APP can be modified to include the O-glycosylation and the like, by Justicidin A. Thus, the effect of Justicidin A to transferrin, internalized by clathrin-dependent endocytosis like APP was measured, in order to identify selectivity of reducing of APP endocytosis rate by O-glycosylation.

Figure 11A:
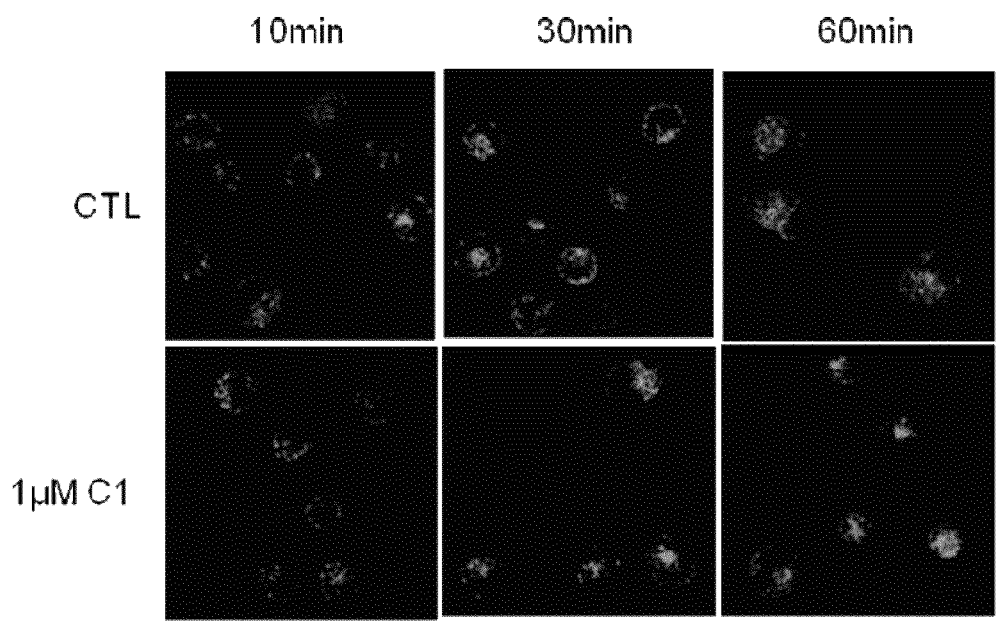
FIGS. 11a and 11b show results of membrane transferring method, slowing of endocytosis rate of APP by Justicidin A, which is selective result by O-glycosylation of APP.

$5 \times 10^5$ cells of HeLa cell line transfected with amyloid precursor protein (APP) same as above, incubated for 24 hrs, 1 uM Justicidin A treated at 4° C. for 45 min. Then, transferrin was fluorescent-labeled by treating Alexa Fluor 488 conjugated transferrin (25 ug/ml concentration, #T13342, Invitrogen). Transferrin endocytosis was progressed depending on the incubation time 10, 30, 60 min at 37° C., then remained transferrin was washed out by treating pH 5.5 buffer (0.1M sodium acetate, 0.05M NaCl) to cell surface for 5 min Intracellular location of transferrin was measured by confocal microscopy (LSM510, Zeiss, Germany) at 488 nm. The test results were shown in FIGS. 11a and 11b. As shown in FIG. 11a, most of transferrin translocated to inside of cell after 10, 30 min, both Justicidin A pre-treated group and untreated control group.

Figure 11B:
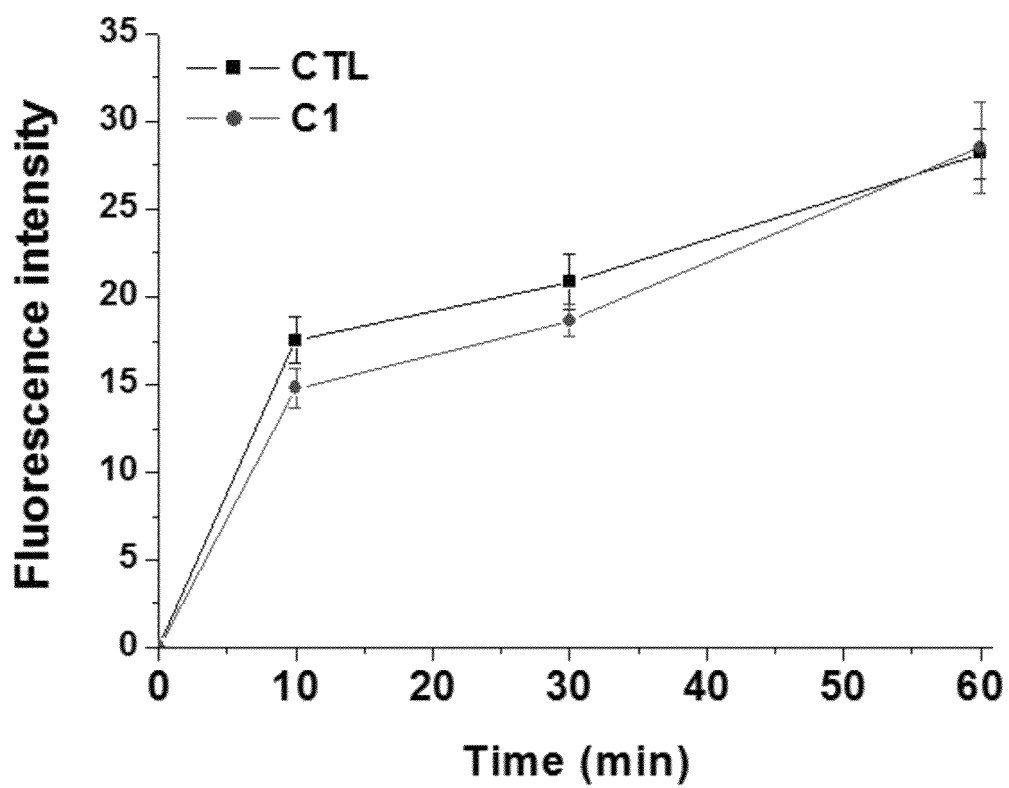

Intracellular location of transferrin APP fluorescent intensity was measured depending on incubation time, the result was shown in FIG. 11b. As shown in FIG. 11b, no effect of Justicidin A to transferrin endocytosis, internalized by clathrin-dependent endocytosis like APP was identified. The effect of Justicidin A to APP endocytosis is selective to APP, not effective to clathrin-dependent endocytosis.

Experimental Example 9

The Effect of Justicidin A Protecting Activity on Cellular Toxicity Caused by Toxic Aβ

This test was carried out in order to identify effect of protecting activity of Justicidin A against cellular toxicity of toxic Aβ.

Firstly, cell viability assay was performed for identifying whether Justicidin A had toxicity to normal brain cell line. Cell viability assay performed using Cell counting kit-8 (CCK-8, WST-8, Kamimashikigun, Kumamoto, Japan). More particularly, $1.5 \times 10^4$ cells of PC12 (Cell No. RCB0009, RIKEN BRC Cell Bank, Tsukuba, Ibaraki, Japan) were seeded to each well of 96-well plate, and incubated for 24 hrs. Then various concentrations of Justicidin A were treated for 24 hrs, and measured by Cell counting kit-8. The result was shown in FIG. 12a.

To identify the protecting effect against cellular toxicity induced by Aβ, PC12 cell was treated with Justicidin A and Aβ25-35 and measured cell viability. More particularly, $1.5 \times 10^4$ cells of PC12 were seeded to each well of 96-well plate, and incubated for 24 hrs. Then, the plate was treated with various concentrations of Justicidin A 30 min, treated 30 uM Aβ25-35, and incubated for 48 hrs. Cell viability was measured by Cell counting kit-8 to show the result FIG. 12b.

Figure 12A:
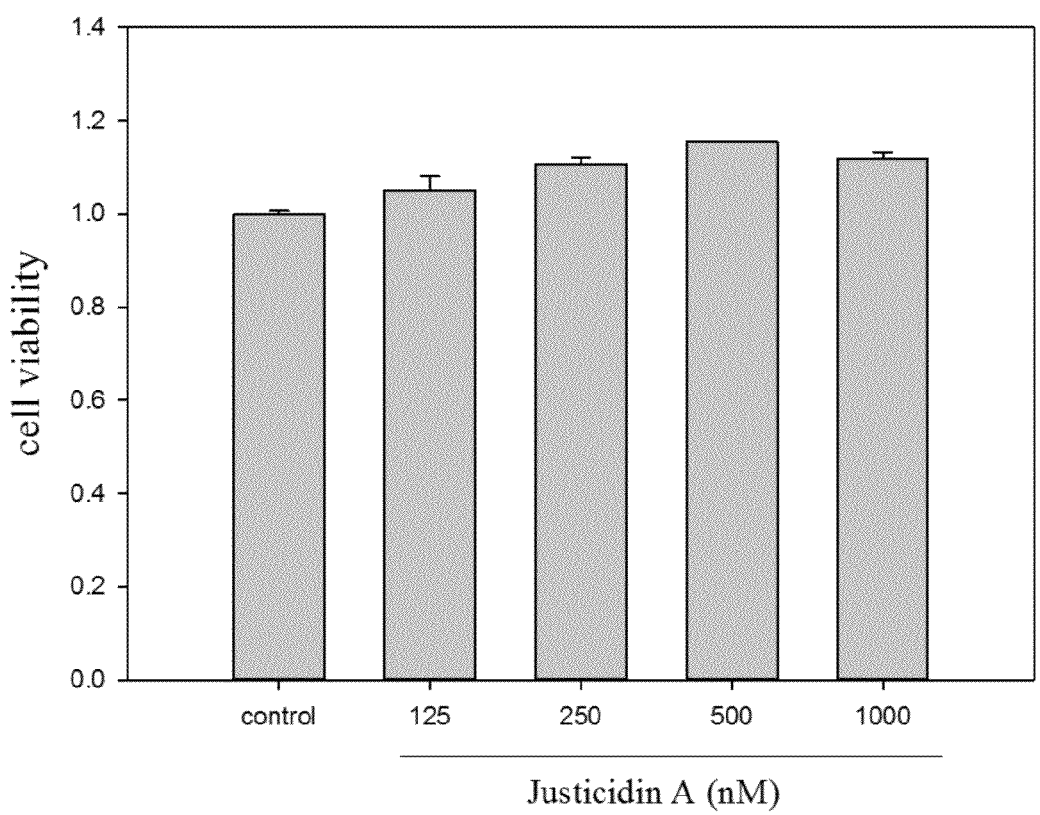
FIGS. 12a and 12b show the toxicity of Justicidin A and reducing of cellular toxicity by $Aβ_{25-35}$.
Figure 12B:
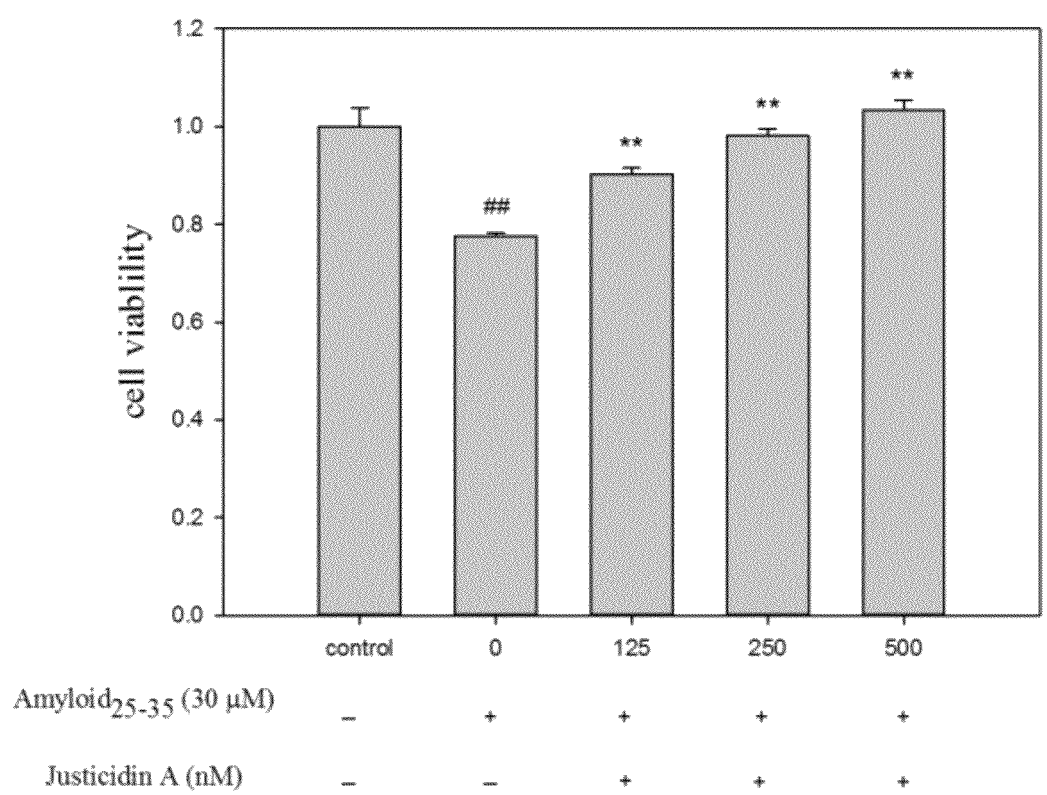

As shown in FIGS. 12a and 12b, Justicidin A has no toxicity to PC12 cell at a concentration of 125 nM to 1000 nM of Justicidin A. Also, Justicidin A reduced the toxicity induced by Aβ25-35 in a concentration-dependent manner.

Experimental Example 10

The Effect of Justicidin a Inhibiting Formation of Aβ Fibril

This test was carried out in order to identify the effect of inhibiting formation of Aβ fibril.

Fibril formation by concentrated Aβ is Alzheimer's representative symptom and has been focused on recently. The concentrated Aβ was measured by Thioflavin T (ThT) fluorescence assay, as chemical process was artificially generated.

For formation of Aβ fibril, Aβ42 was melt in 1,1,1,3,3,3-hexafluoro-2-propanol (HFIP) up to 1 mg/ml, then injected to 96-well plate, the concentration of Aβ42 was 10 uM each well, HFIP was evaporated shortly before the beginning of the experiment. Various concentrations of Justicidin A and a certain amount of 5 uM ThT were added, and Fluorescence intensity was measured at various times by Tecan infinite M1000 microplate reader (Tecan, Switzerland). The result was shown in FIG. 13.

Figure 13:
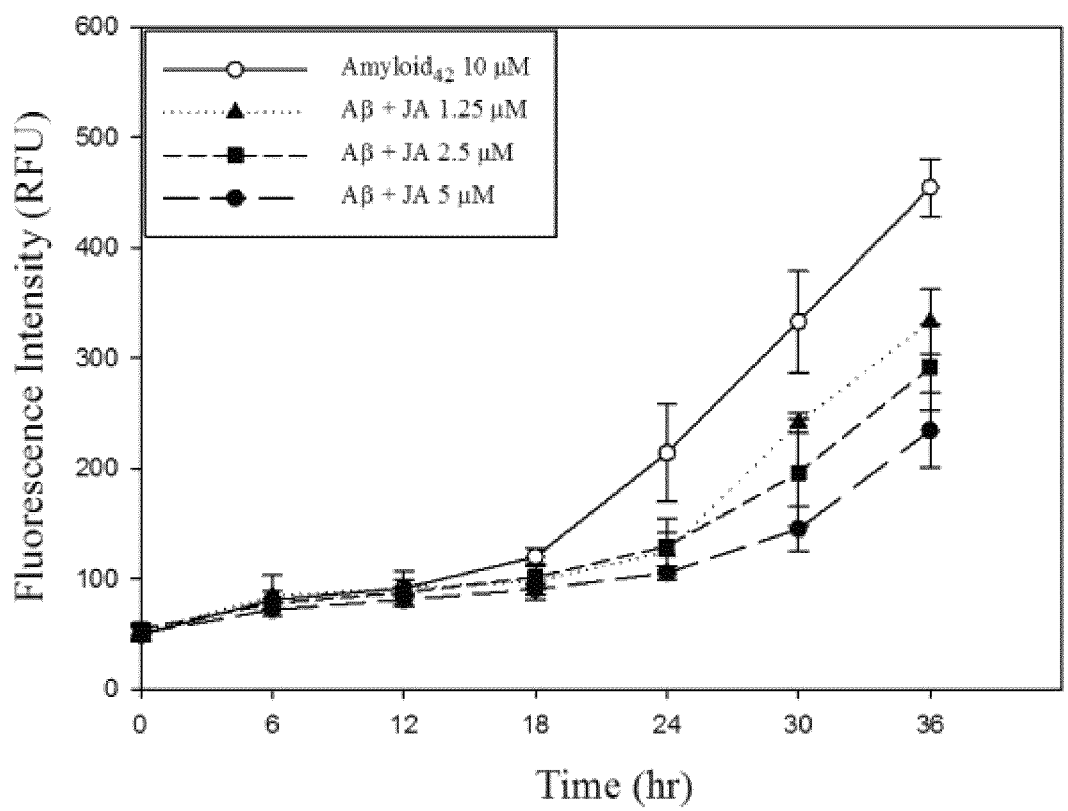
FIG. 13 is a graph showing the effect of inhibiting of formation of Aβ fibril by Justicidin A.

As shown in FIG. 13, the result confirmed that Justicidin A inhibited the formation of Aβ fibril in a concentration-dependent manner up to 36 hrs. Specially, the group treated with 5 uM Justicidin A inhibited the formation of Aβ fibril by 52%, compared to the control group.

Experimental Example 11

The Effect of Justicidin A on Ameliorating the Memory Impairment

<11-1> Morris Water Maze Test Justicidin A

To test the improvement of Justicidin A (C1) obtained in Example 2 in impaired memory driven with scopolamine treatment, Morris water maze test was performed by using the model mouse.

The male ICR mouse was 5 to 6-week age (25-30 g of body weight) (Orientbio Inc., Seougnam, Republic of Korea), and was raised with solid feed and tap water for 1 week before being used for test. At a first day, the normal control group and the group administered by the scopolamine were fed with 5% (v/v) DMSO-saline, the test group was orally administered by 1, 5, 10 and 20 mg/kg/10 ml of Justicidin A (C1) in 5% DMSO-Saline, and the comparative group was administered with 2 mg/kg/10 ml of Donepezil (brand name: Aricept, Eisai) being commercially available as a drug for treating an dementia of the Alzheimer's type. After 30 minutes, the groups were intraperitoneally injected by scopolamine (Sigma-Aldrich Chemical Co., St Louis, USA) at 1 mg/kg/10 ml. after 30 minutes of scopolamine injection, the mice were dropped in circular water bath (diameter 120 cm, height 50 cm) filled with black water and hidden escape platform, and were left to freely swim and seek the platform for 90 seconds. Various labels with different color and shape which the mice could see as a target were equipped in the water bath, and the water temperature was adjusted at a room temperature. In case that the mouse sought and set on the escape platform for 5 seconds, the test was finished.

The same test was performed repetitively twice per a day for 4 days as an Acquisition Test, and the entire test was automatically recorded and analyzed with Noldus Ethovision 7.0 program (Noldus Information Technology, USA). The time when the mice sought the platform during the Acquisition Test was shown in FIG. 14.

In addition, after finishing the Acquisition Test performed for four (4) days, the Probe test was carried out at fifth day. The mice were dropped in the same circular water bath except that the hidden escape platform was removed, and were left to freely swim to seek the platform for 120 seconds. The whole test procedure was automatically recorded and analyzed with Noldus Ethovision 7.0 program (Noldus Information Technology, USA). The time when the mice swam in the part of platform used to be was measured and shown in FIG. 15.

Figure 14:
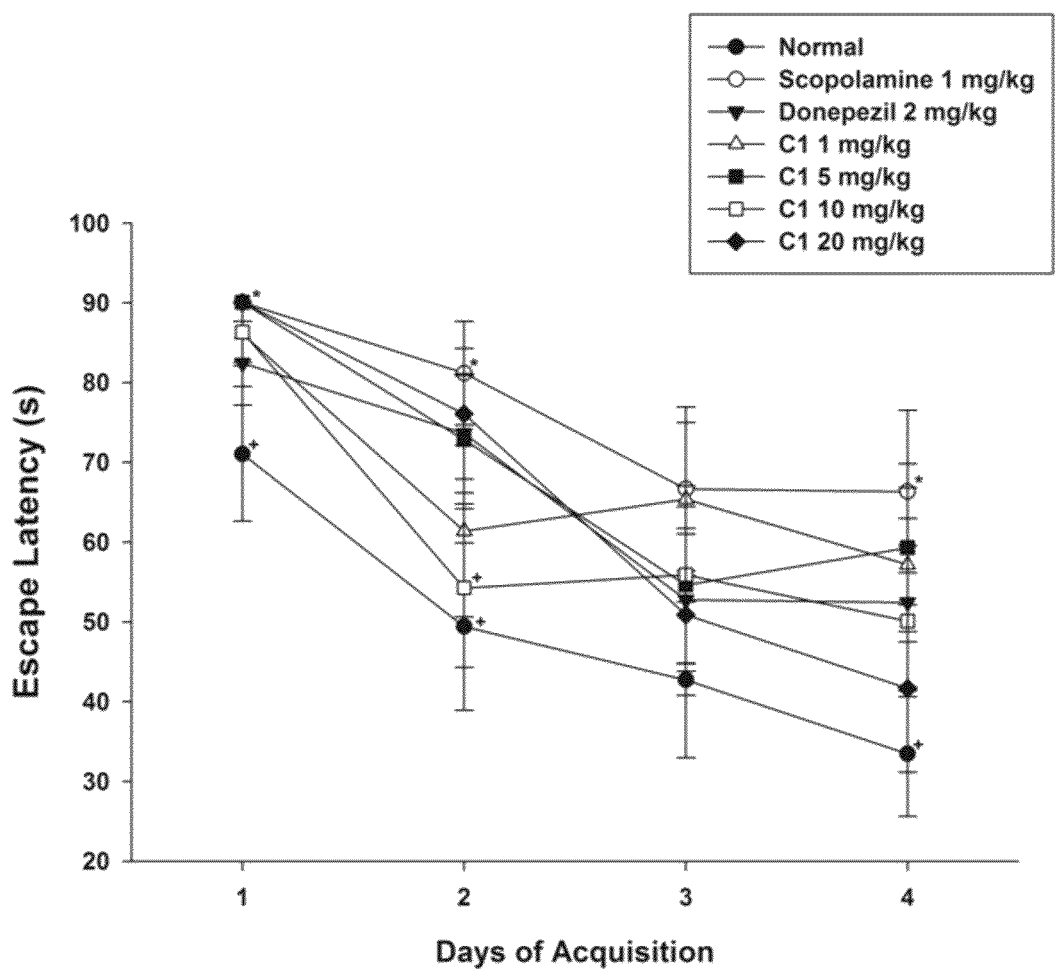
FIG. 14 is a graph showing the effect of improving the memory obtained from acquisition test for four days of Morris water-maze test using the model mouse with impaired memory driven with scopolamine treatment, at various concentrations of administered Justicidin A (C1).
Figure 15:
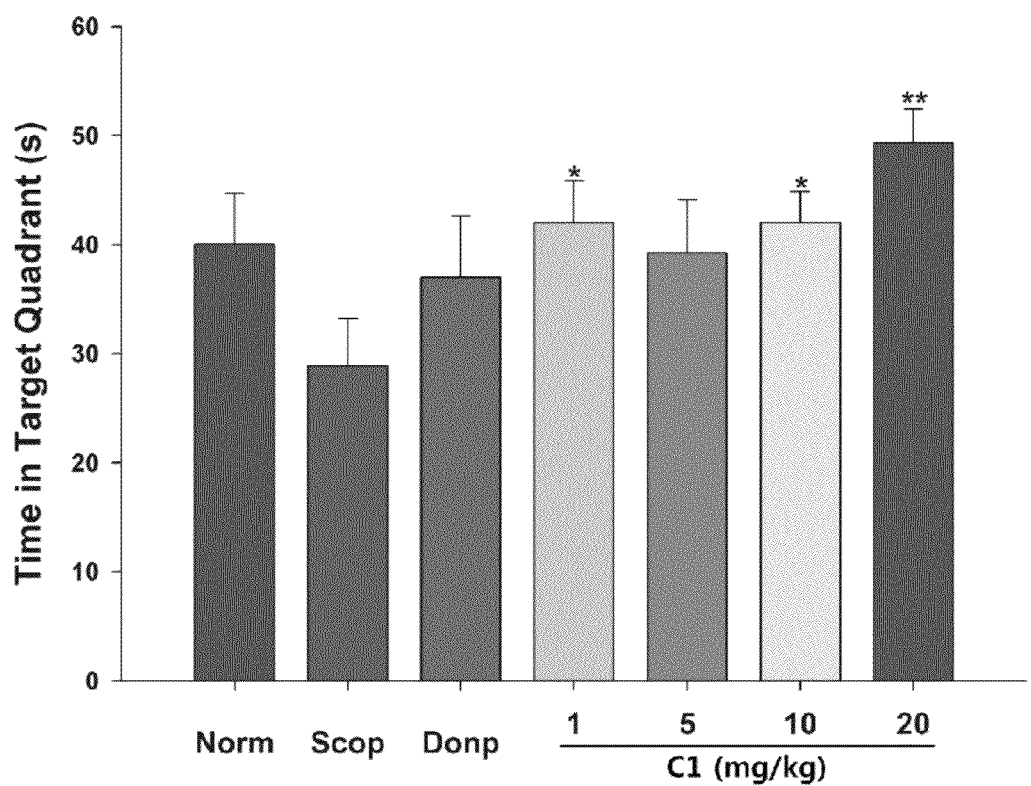
FIG. 15 is a graph showing the effect of improving the memory obtained from probe test at fifth day of Morris water-maze test using the model mouse with impaired memory driven with scopolamine treatment, at various concentrations of administered Justicidin A (C1).

As shown in FIG. 14 and FIG. 15, only the group treated with oral administration of Justicidin A represented the equivalent or higher memory and learning ability, compared to the negative control of the group administered by the scopolamine.

<11-2> The Effect of Ameliorating the Memory Impairment on Novel Object Recognition Test of Justicidin A To test whether Justicidin A (C1) obtained in Example 2 inhibits the memory loss driven with scopolamine treatment, Novel object recognition test was performed by using the model mouse.

The male ICR mouse was 5 to 6-week age (25~30 g of body weight) (Orientbio Inc., Seougnam, Republic of Korea), and was raised with solid feed and tap water for 1 week before being used for test. For 3 days before the test, each mouse to get adjusted to Arena (grey mat acryl material, 50 cm×50 cm×60 cm) went freely into the Arena for 10 minutes per a day.

At a first day, the normal control group and the group administered by the scopolamine were fed with 5% (v/v) DMSO-saline, the test group was orally administered by 1, 5, 10 and 20 mg/kg/10 ml of Justicidin A (C1) in 5% DMSO-Saline, and the comparative group was administered with 2 mg/kg/10 ml of Donepezil (brand name: Aricept, Eisai) being commercially available as a drug for treating an dementia of the Alzheimer's type. After 30 minutes, the groups were intraperitoneally injected by scopolamine (Sigma-Aldrich Chemical Co., St Louis, USA) at 1 mg/kg/10 ml. After 30 minutes of scopolamine injection, the mice were dropped in the Arena. After being adjusted for 5 minutes, two identical objects with same shape, color and size were dropped in the Arena and thus, the mice sought the objects for 3 minutes and then the test was finished.

Figure 16:
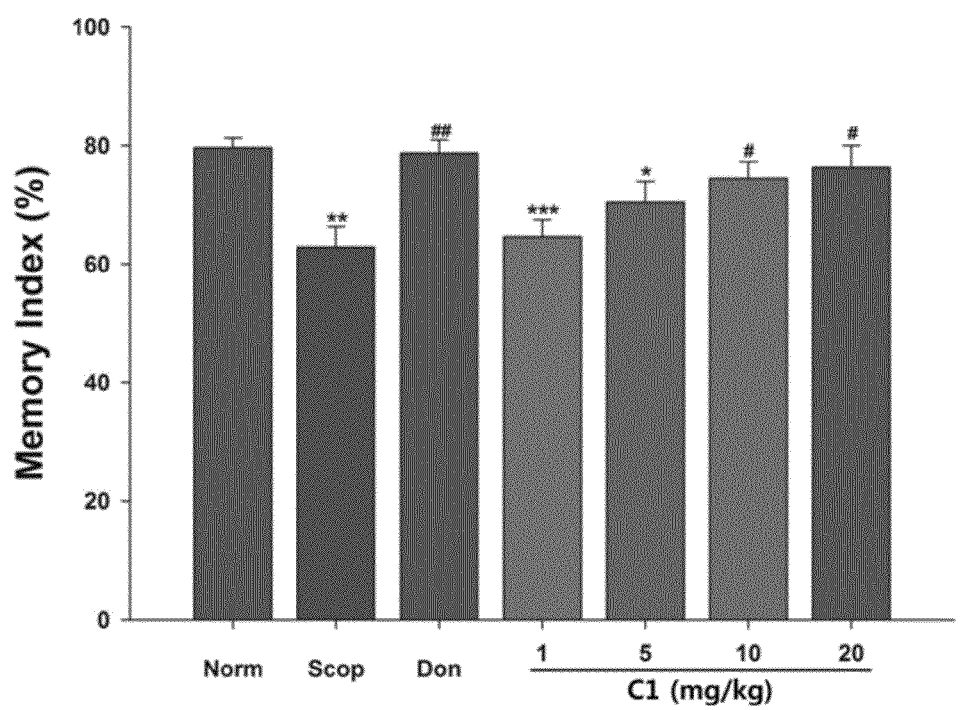
FIG. 16 is a graph showing the effect of improving the memory obtained from Novel object recognition test using the model mouse with impaired memory driven with scopolamine treatment, at various concentrations of administered Justicidin A (C1).

At the second day, the mice were dropped into the Arena without treatment of additional drug and scopolamine. After adapting in the Arena for 5 minutes, the object to be used at the previous day and an object with different shape and color were added to the Arena simultaneously to let the mice seek them freely for 3 minutes and then the test was completed. Entire test was automatically recorded and analyzed with Noldus Ethovision 7.0 program (Noldus Information Technology, USA). The time when the mice sought the object in 3 minutes after dropping two objects at second day of test were measured and calculated as Memory Index (%, ratio of time for Novel object recognition to entire time for recognition). The result was indicated in FIG. 16. In FIG. 16, the term 'Norm' refers to the normal group, and the term 'Scop' refers to the negative control with treatment of only scopolamine.

As indicated in FIG. 16, the test group with oral administration of 10 mg/kg and 20 mg/kg of Justicidin A showed high memory and learning ability which was similar to that of the positive group administered with 2 mg/kg of Donepezil.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method inhibiting formation of β-amyloid in a human brain, comprising:
administering a therapeutically effective amount of arylnaphthalene lignan derivatives and pharmaceutically acceptable salts thereof, to a human in need of treatment of a condition associated with the formation of β-amyloid in the human brain to increase the amyloid precursor protein sAPPα and thereby decrease β-amyloid production,
wherein the condition is selected from the group consisting of dementia and Alzheimer's disease, and
wherein the arylnaphthalene lignan derivatives are at least one selected from the group consisting of 5-methoxyjusticidin A represented by Chemical Formula 1, and Chinensinaphthol represented by Chemical Formula 2:

Chemical Formula 1

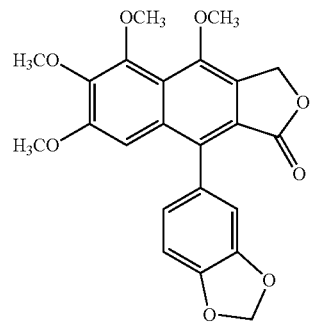

Chemical Formula 2

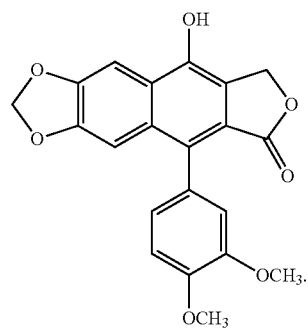

* * * * *